United States Patent
Eto et al.

(10) Patent No.: US 11,136,547 B2
(45) Date of Patent: Oct. 5, 2021

(54) MESODERM INDUCTION METHOD HAVING HIGH BLOOD CELL DIFFERENTIATION CAPACITY

(71) Applicants: Kyoto University, Kyoto (JP); Megakaryon Corporation, Kyoto (JP)

(72) Inventors: Koji Eto, Kyoto (JP); Hiroshi Endo, Kyoto (JP); Yukitaka Ito, Kyoto (JP); Junichi Fukunaga, Kyoto (JP)

(73) Assignees: Kyoto University, Kyoto (JP); Megakaryon Corporation, Kyoto (JP)

( * ) Notice: Subject to any disclaimer, the term of this patent is extended or adjusted under 35 U.S.C. 154(b) by 198 days.

(21) Appl. No.: 16/083,503

(22) PCT Filed: Mar. 22, 2017

(86) PCT No.: PCT/JP2017/011543
§ 371 (c)(1),
(2) Date: Sep. 8, 2018

(87) PCT Pub. No.: WO2017/164257
PCT Pub. Date: Sep. 28, 2017

(65) Prior Publication Data
US 2019/0071636 A1     Mar. 7, 2019

(30) Foreign Application Priority Data
Mar. 23, 2016 (JP) .............................. JP2016-058781

(51) Int. Cl.
| | |
|---|---|
| *A61K 35/19* | (2015.01) |
| *A61K 35/28* | (2015.01) |
| *A61K 35/545* | (2015.01) |
| *C12N 5/0735* | (2010.01) |
| *C12N 5/078* | (2010.01) |
| *C12N 5/00* | (2006.01) |
| *C12N 5/10* | (2006.01) |
| *C12N 15/09* | (2006.01) |
| *A61P 7/08* | (2006.01) |
| *A61K 38/18* | (2006.01) |
| *C12N 5/074* | (2010.01) |

(52) U.S. Cl.
CPC ............ *C12N 5/0606* (2013.01); *A61K 35/19* (2013.01); *A61K 38/1875* (2013.01); *A61P 7/08* (2018.01); *C12N 5/0031* (2013.01); *C12N 5/0607* (2013.01); *C12N 5/0644* (2013.01); *C12N 5/10* (2013.01); *C12N 15/09* (2013.01); *C12N 2500/99* (2013.01); *C12N 2501/115* (2013.01); *C12N 2501/15* (2013.01); *C12N 2501/155* (2013.01); *C12N 2501/16* (2013.01); *C12N 2501/165* (2013.01); *C12N 2501/415* (2013.01); *C12N 2506/02* (2013.01)

(58) Field of Classification Search
None
See application file for complete search history.

(56) References Cited

U.S. PATENT DOCUMENTS

| | | |
|---|---|---|
| 2013/0011924 A1 | 1/2013 | Niwa |
| 2013/0209416 A1 | 8/2013 | Ma |
| 2016/0122719 A1 | 5/2016 | Ma |
| 2016/0186135 A1* | 6/2016 | Thomson ............... C12N 5/069 435/29 |

FOREIGN PATENT DOCUMENTS

| | | |
|---|---|---|
| JP | 2013-521762 A | 6/2013 |
| JP | 2013-531497 A | 8/2013 |
| WO | 2014161075 A1 | 10/2014 |

OTHER PUBLICATIONS

Kennedy et al., Development of the hemangioblast defines the onset of hematopoiesis in human ES cell differentiation cultures Blood. 2007; 109:2679-2687.*
International Search Report received in PCT/JP2017/011543 dated Jun. 6, 2017.
Written Opinion received in PCT/JP2017/011543 dated Jun. 6, 2017.
Kardel et al., "Modeling human hematopoietic cell development from pluripotent stem cells", Apr. 14, 2012, pp. 601-611, vol. 40, No. 8, Publisher: Experimental Hematology.
MacLean et al., "Altered hematopoiesis in trisomy 21 as revealed through in vitro differentiation of isogenic human pluripotent cells", Oct. 23, 2012, pp. 17567-17572, vol. 109, No. 43, Publisher: PNAS USA.
Evseenko et al., "Mapping the first stages of mesoderm commitment during differentiation of human embryonic stem cells", Aug. 3, 2010, pp. 13742-13747, vol. 107, No. 31, Publisher: PNAS USA.
Nakagawa, et al., "Two differential flows in a bioreactor promoted platelet generation from human pluripotent stem cell-derived megakaryocytes", Apr. 22, 2013, pp. 742-748, vol. 41, No. 8, Publisher: Exp Hematol.
Pick et al., "Generation of megakaryocytic progenitors from human embryonic stem cells in a feeder- and serum-free medium", 2013, p. e55530, vol. 8, No. 2, Publisher: PLoS One.
Tan et al., "Efficient derivation of lateral plate and paraxial mesoderm subtypes from human embryonic stem cells through GSKi-mediated differentiation", Jul. 1, 2013, pp. 1893-1906, vol. 22, No. 13, Publisher: Stem Cells Dev.
Yu et al., "APELIN promotes hematopoiesis from human embryonic stem cells", Jun. 28, 2012, pp. 6243-6254, vol. 119, No. 26, Publisher: Blood.

* cited by examiner

*Primary Examiner* — Maria G Leavitt
(74) *Attorney, Agent, or Firm* — Suzannah K Sundby, Esq.; Canady + Lortz LLP

(57) ABSTRACT

Provided is a method for inducing mesoderm, comprising a step of bringing pluripotent stem cells into contact with bone morphogenetic protein 4 (BMP4) or CHIR for at least 3 days.

6 Claims, 15 Drawing Sheets

Specification includes a Sequence Listing.

Fig. 3
A
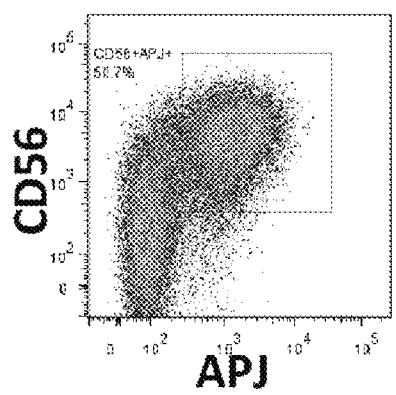
B
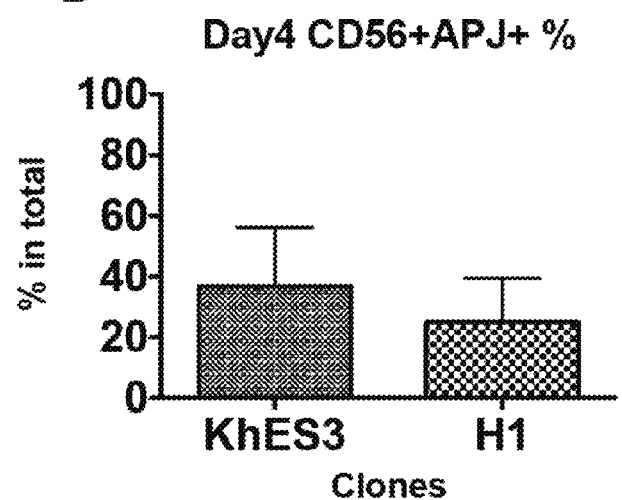
C
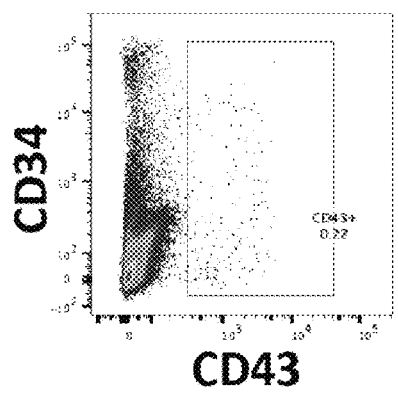
D
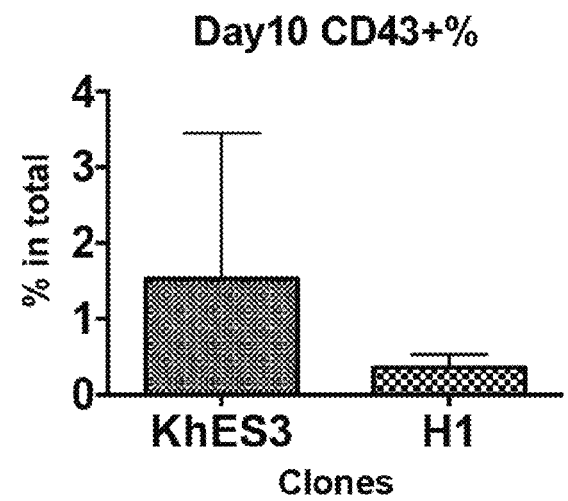

Fig. 6
A
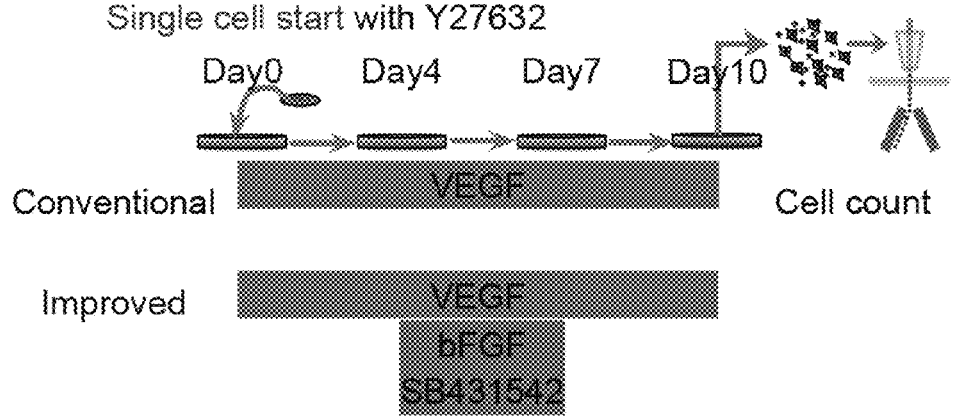
B
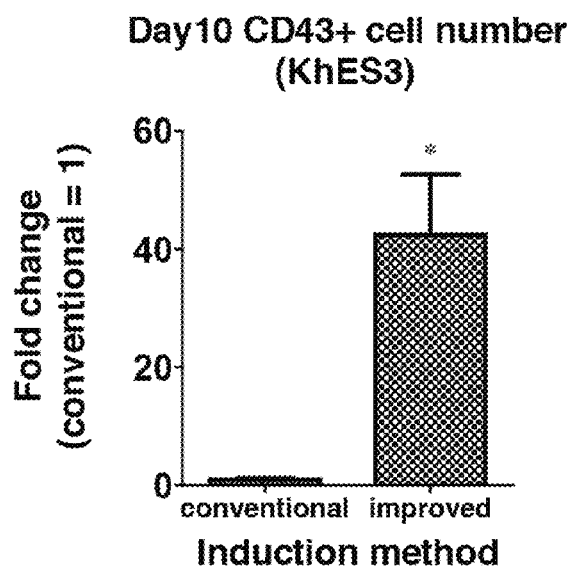
C
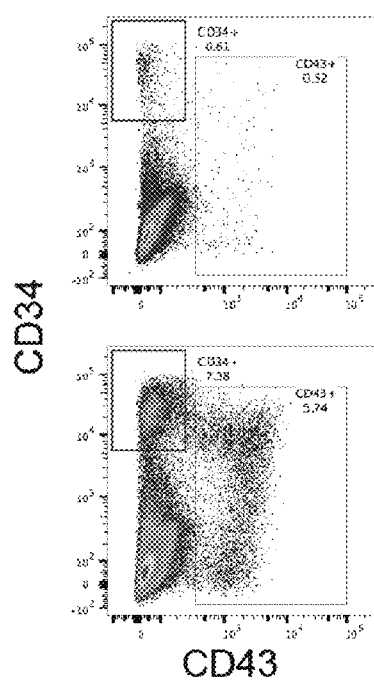

Fig. 10
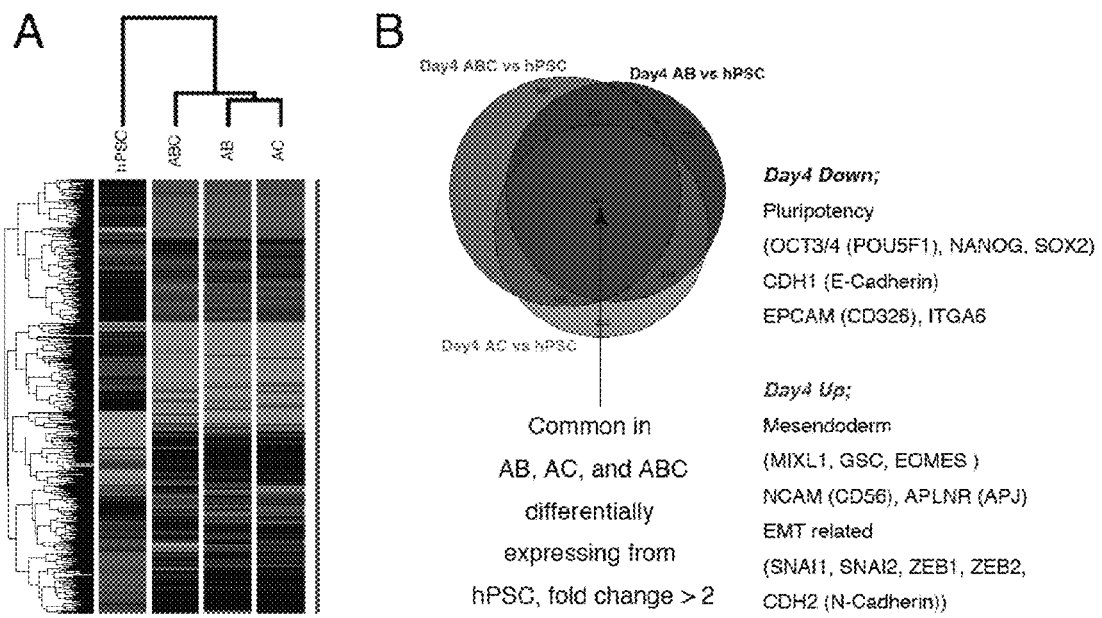
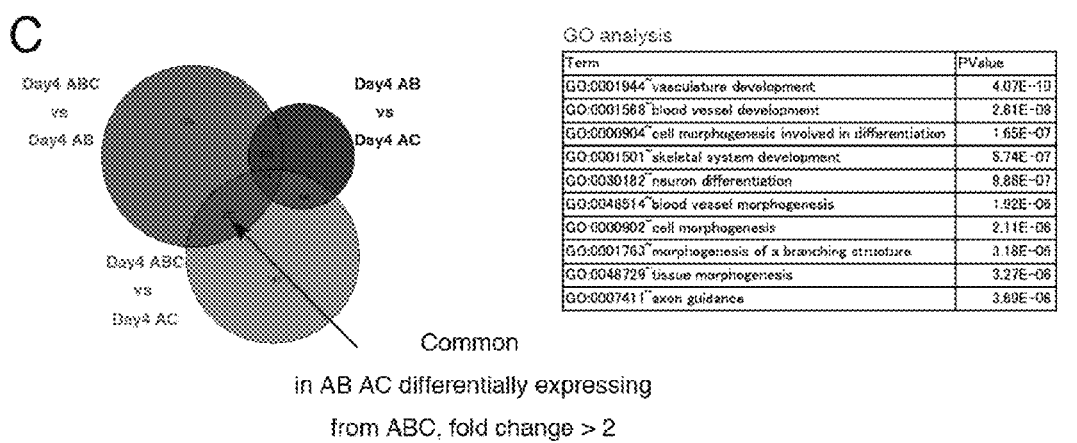
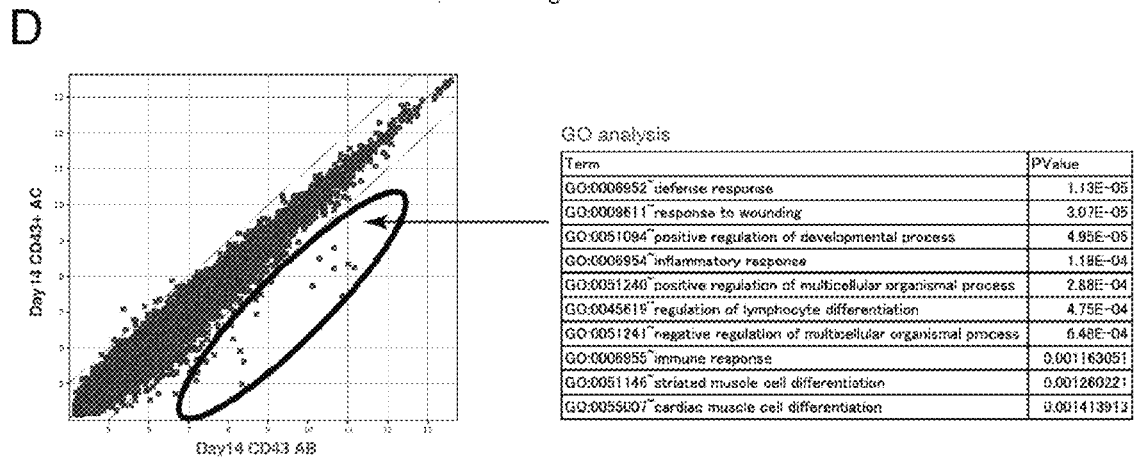

Fig. 11 Cont.
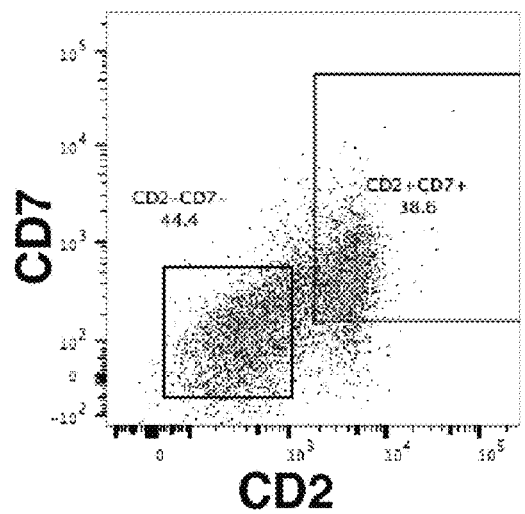
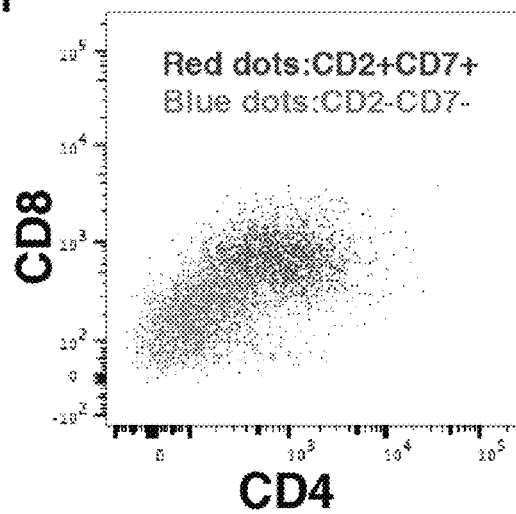
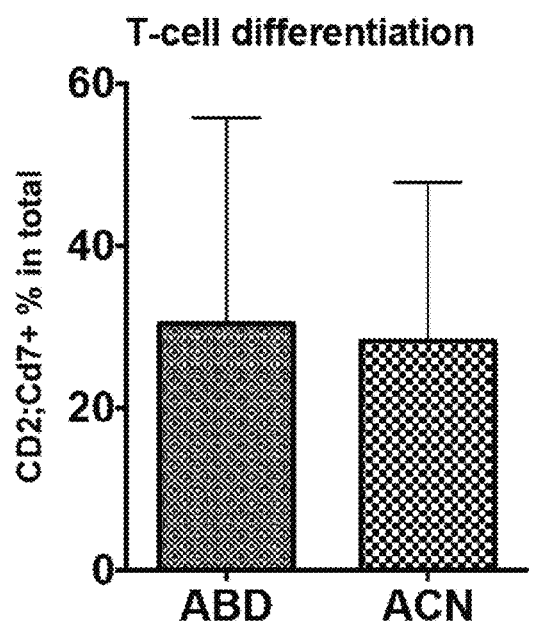

MESODERM INDUCTION METHOD HAVING HIGH BLOOD CELL DIFFERENTIATION CAPACITY

TECHNICAL FIELD

The present invention relates to a novel mesoderm induction method, and relates in particular to a method for inducing mesoderm with high blood cell differentiation ability from human pluripotent stem cells, and to a method for producing megakaryocytes and platelets using the same.

BACKGROUND ART

A supply of blood cells for treatment is considered necessary when performing surgical treatment or treatment for blood-related diseases. There is especially strong demand for platelets and proplatelets, which are essential for blood coagulation (hemostasis), and also for megakaryocytes because they produce platelets. Platelets are in special demand for leukemia treatment, bone marrow transplants, anti-cancer treatment and the like, and a stable supply is essential.

Pluripotent stem cells such as ES cells and iPS cells are used as a cell source in the artificial production of blood cells including platelets. However, although there have been scattered reports on differentiation lineages and mechanisms for producing hematopoietic mesoderm from pluripotent stem cells, no conclusions have been reached (Non-Patent Document 1).

CITATION LIST

Non-Patent Document

Non-Patent Document 1: Kardel M D, Eaves C J, Modeling Human Hematopoietic Cell Development from Pluripotent Stem Cells. Experimental Hematology. 2012 Apr. 14; 40(8):601-11

SUMMARY

Technical Problem

Three humoral factor groups, Nodal/Activin A/TGFβ, WNT3 and BMP4, are known to play an important role in mesoderm formation in mouse development, but the signals controlling detailed cell lineages in human development have heretofore been unknown.

Elucidating the differentiation lineages and mechanisms leading from human pluripotent stem cells to mesodermal cells could also contribute to efforts to induce differentiation of blood cell groups.

Solution to Problem

The inventors perfected the present invention after discovering that BMP4 or CHIR plays an important role in the differentiation of hematopoietic mesoderm from human pluripotent stem cells.

That is, the present application encompasses the following inventions.

[1] A method for inducing mesoderm, comprising a step of bringing pluripotent stem cells into contact with bone morphogenetic protein 4 (BMP4) or CHIR for at least 3 days.

[2] The method according to [1], wherein the pluripotent stem cells are also brought into contact with Activin A.

[3] The method according to [1] or [2], wherein the mesoderm comprises cells that are both CD56-positive and APJ-positive.

[4] The method according to any one of [1] to [3], further comprising a step of bringing the CD56-positive, APJ-positive cells into contact with VEGF, bFGF and a TGFβ inhibitor.

[5] The method according to any one of [1] to [4], wherein the contact step is performed under serum-free and/or feeder-free conditions.

[6] A method for producing a culture containing megakaryocytes and megakaryocyte precursor cells, comprising a step of inducing differentiation of megakaryocyte cells from mesoderm induced by the method according to any one of [1] to [5].

[7] A method for producing platelets from megakaryocytes produced by the method according to [6].

[8] A platelet preparation containing platelets produced by the method according to [7].

[9] A method for transplanting or transfusing platelets produced by the method according to [7] into a test subject.

Advantageous Effects of Invention

With the novel differentiation induction method of the invention using BMP4 or CHIR, not only can pluripotent stem cells be induced to differentiate more efficiently into mesoderm, but differentiation induction into blood cell groups can also be promoted. The present invention also makes it possible to efficiently induce differentiation not only of megakaryocyte cells and platelets, but also of various blood cells including hematopoietic stem cells.

BRIEF DESCRIPTION OF DRAWINGS

FIG. 3A shows a FACS plot on the 4th day of differentiation. FIG. 3B shows the average and standard deviation (n=3) of the ratio of CD56+APJ+ cells in two human ES cell lines. FIG. 3C shows a FACS plot on the 10th day of differentiation. FIG. 3D shows the average and standard deviation (n=3) of the ratio of CD43+ cell in two human ES cell lines.

FIG. 6A shows an outline of an experiment showing that blood cell differentiation efficiency was dramatically improved by intervention in the intermediate step. Because this was based on the number of blood cells ultimately obtained, the initial sowing numbers had to be uniform under the different conditions. Differentiation was therefore initiated with single cells. FIG. 6B shows that bFGF and SB431542 had a synergistic effect, resulting in a roughly 40-fold increase in blood cell production in comparison with existing reports. The KhES3 data represent average plus standard deviation (n=5, *p<0.05, paired t-test). FIG. 6C shows a FACS plot of all differentiated cells induced by the conventional and improved methods. Most of the differentiated cells obtained by the conventional method were CD43 negative, but the percentage of CD43+ cells was increased in the improved method. KhES3 data are shown.

FIG. 10A shows differences discovered among the various conditions in gene expression pattern analysis. Gene expression analysis was performed on the day 0 hPSC cells and the day 4 CD56+APJ+ cells induced under the AB, AC and ABC conditions, the day 4 cells under each condition were compared with the hPSC cells, and gene groups with a fold change greater than 2 were extracted and subjected to clustering analysis. FIG. 10B is a Venn's diagram constructed of gene groups of Fold change >2 in a comparison of day 4 CD56+APJ+ cells and hPSC among the conditions. Gene groups that differed under all conditions included a gene group associated with pluripotency, a gene group associated with mesoderm, and a gene group associated with EMT. FIG. 10C is a Venn's diagram constructed of gene groups of Fold change >2 in a comparison of day 4 CD56+APJ+ cells among the conditions. Gene groups that showed differed among the AB, AC and ABC conditions were subjected to GO analysis. The Top 10 terms are shown in the table. Differences were confirmed in gene groups associated with tissues other than blood cells and blood vessels. FIG.

10D shows a comparative analysis of induction of day 14 CD43+ cells induced under the AB and AC conditions. Gene groups that exhibited AB− preferential variation were subjected to GO analysis. The TOP 10 terms are shown in the table. Variation was confirmed in immune-associated gene groups.

FIG. 11A gives an outline of an experiment showing that there was no difference between the AB and AC conditions in the potency of induced blood cells using KhES3 cells. In the initial step, mesoderms induced under the two conditions were differentiated into blood cells, and the resulting blood cells were used in assays. FIG. 11B shows the results of a colony-forming ability assay (n=3), (G: Granulocyte colony, M: Macrophage colony, GM: Granulocyte+Macrophage colony, E: Erythroid colony, Mix: E+G or E+M or E+GM). No significant differences were found between the numbers of each kind of colony. FIG. 11C shows results for erythroid differentiation. A CD41−CD235+ erythroid population was confirmed by FACS under all conditions (C), and there were no significant differences in differentiation efficiency (D) (n=3, paired t-test). FIG. 11D shows results for erythroid differentiation. A CD41−CD235+ erythroid population was confirmed by FACS under all conditions (C), and there were no significant differences in differentiation efficiency (D) (n=3, paired t-test). FIG. 11E shows results for megakaryocyte differentiation. A CD41+CD42b+ megakaryocyte population was confirmed by FACS under all conditions (E), and there were no significant differences in differentiation efficiency (F) (n=3, paired t-test). FIG. 11F shows results for megakaryocyte differentiation. A CD41+CD42b+ megakaryocyte population was confirmed by FACS under all conditions (E), and there were no significant differences in differentiation efficiency (F) (n=3, paired t-test).

FIG. 11G shows results for T-cell differentiation. A CD2+ CD7+ cell population was confirmed under all conditions (G), and all of the CD2+CD7+ cells (red dots) were also CD4+CD8+ (H). There were no significant differences in the differentiation efficiency (I) (n=3, paired t-test). FIG. 11H shows results for T-cell differentiation. A CD2+CD7+ cell population was confirmed under all conditions (G), and all of the CD2+CD7+ cells (red dots) were also CD4+CD8+ (H). There were no significant differences in the differentiation efficiency (I) (n=3, paired t-test). FIG. 11I shows results for T cell differentiation. A CD2+CD7+ cell population was confirmed under all conditions (G), and all of the CD2+CD7+ cells (red dots) were also CD4+CD8+ (H). There were no significant differences in the differentiation efficiency (I) (n=3, paired t-test).

Figure 12:
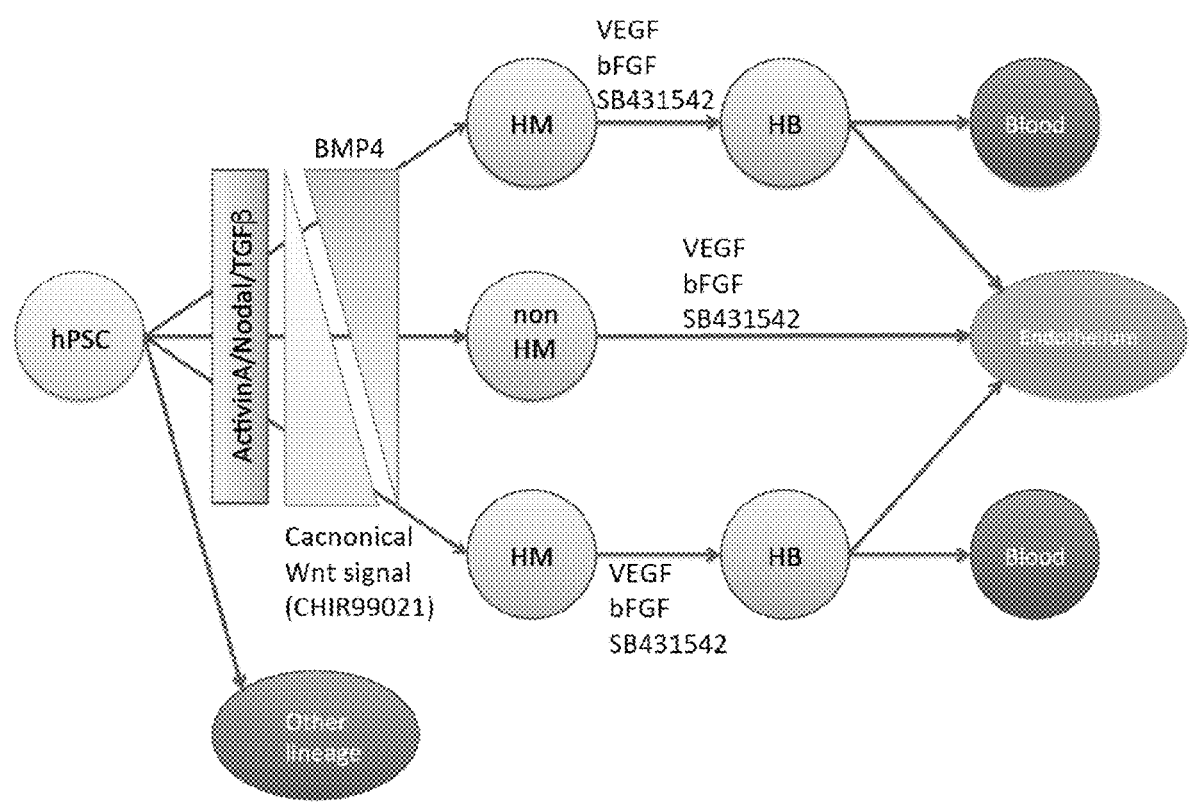

FIG. 12 shows a summary of the experimental results from the examples. In the presence of Activin A, hematopoietic mesoderm was differentiated by intervention with either BMP4 or canonical WNT signal, and subsequently differentiated into blood cells with high efficiency under appropriate conditions (in the presence of VEGF, bFGF and SB431542). However, when both BMP4 and canonical WNT signal were added in the presence of Activin A, the differentiated mesoderm had the potential to become vascular endothelium but not blood cells (HM: Hematopoietic mesoderm, HB: Hemangioblast, hPSC: human pluripotent stem cell).

Figure 13:
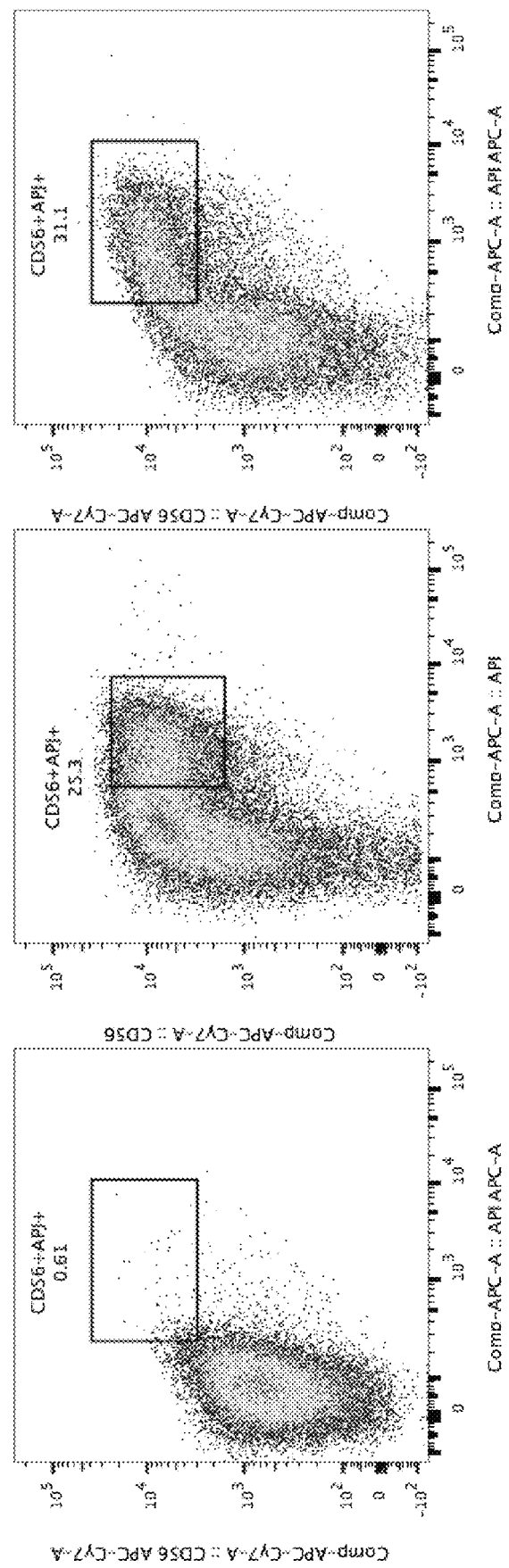

FIG. 13 shows the results of a comparison of expression patterns in day 4 CD56+APJ+ cells obtained by adding Activin A alone, Activin A and BMP4, or Activin A and CHIR.

Figure 14:
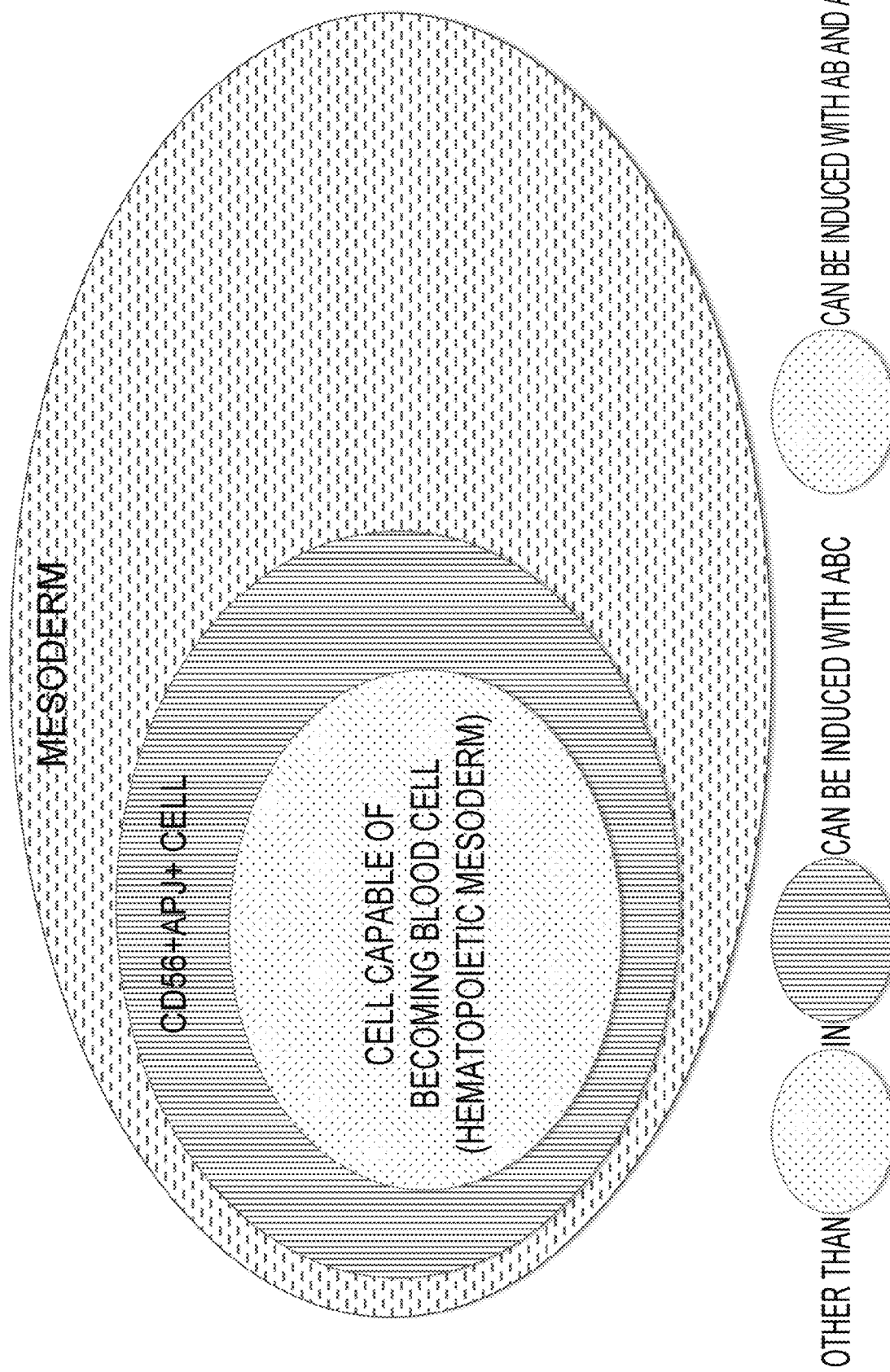

FIG. 14 is an image relating to the definition of mesoderm.

DESCRIPTION OF EMBODIMENTS (Mesodermal Cell Producing Method)

The mesodermal cell producing method of the present invention comprises a step of bringing pluripotent stem cells into contact with BMP4 or CHIR for 3 days. As used in this Description, the term "mesoderm" or "mesodermal cell" refers to a cell that is CD56-positive and APJ-positive. The mesoderm induced by the present invention consists of CD56-positive, APJ-positive cells that also have high blood cell differentiation ability (FIG. 14).

In the present invention, pluripotent stem cells are stem cells having pluripotency that allows them to differentiate into all cells in the living body and also having proliferation ability, and include for example embryonic stem (ES) cells (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165), embryonic stem cells from cloned embryos obtained by nucleus transplantation (ntES cells) (T. Wakayama et al. (2001), Science, 292:740-743; S. Wakayama et al. (2005), Biol. Reprod., 72:932-936; J. Byrne et al. (2007), Nature, 450:497-502), sperm stem cells ("GS cells") (M. Kanatsu-Shinohara et al. (2003) Biol. Reprod., 69:612-616; K. Shinohara et al. (2004), Cell, 119:1001-1012), embryonic germ cells ("EG cells") (Y. Matsui et al. (1992), Cell, 70:841-847; J. L. Resnick et al. (1992), Nature, 359:550-551), artificial pluripotent stem (iPS) cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666), and pluripotent cells from cultured fibroblasts and bone marrow stem cells (Muse cells) (WO 2011/007900) and the like. The pluripotent stem cells are more preferably human pluripotent stem cells.

Pluripotent stem cells can be induced to differentiate into mesodermal cells by bringing them into contact for the desired amount of time with the bone morphogenetic factor BMP4 or with CHIR (CHIR-99021 or CHIR-98014), which is known as a GSK-3β inhibitor or Wnt signaling activator. BMP4 or CHIR is brought into contact with the pluripotent stem cells by adding it to medium or the like for culturing the pluripotent stem cells. The use of another GSK-3β inhibitor (such as 3F8, A1070722, AR-A014418, BIO, BIO-acetoxime, 10Z-Hymenialdisine, Indirubin-3'-oxime, Kenpaullone, L803, L803-mts, MeBIO, NSC 693868, SB216763, SB415286, TC-G 24, TCS 2002, TCS 21311 or TWS 119 etc) instead of CHIR is intended by another embodiment of the invention. The medium may also contain other ingredients, such as Activin A or other ingredients necessary for inducing differentiation into mesodermal cells. The culture conditions are preferably serum-free and/or feeder-free conditions. The period of contact is preferably at least 3 days, such as 3 to 5 days or especially 3 to 4 days.

The mesodermal cells obtained through this contact step are CD56-positive and APJ-positive. CD56 and APJ have each been reported independently as mesodermal markers (Evseenko, D. et al. P Natl Acad Sci USA 107, 13742-13747 (2010); Vodyanik, M. A. et al. Cell stem Cell 7, 718-729 (2010); Yu, Q. C. et al. Blood 119, 6243-6254 (2012)). CD56 is an adhesion factor also known as NCAM. APJ is a functional molecule that has been reported as a receptor (APLNR) for Apelin molecules and the like.

The CD56-positive, APJ-positive cells may also be further brought into contact with vascular endothelial growth factor (VEGF), basic fibroblast growth factor (bFGF), and a transforming growth factor beta (TGFβ) inhibitor to thereby improve the differentiation efficiency of hemangioblasts from mesoderm. For example, cells that are CD56 positive and APJ positive can produce blood cells more efficiently than cells that are CD56 negative and APJ negative. An example of a TGFβ inhibitor is SB431542.

(Method for Producing Culture Containing Megakaryocytes or Megakaryocyte Precursor Cells)

A method for producing a culture containing megakaryocytes or megakaryocyte precursor cells in the present invention comprises a step of inducing differentiation of megakaryocyte cells from mesodermal cells produced by the above methods.

The medium used in the invention is not particularly limited, but may be prepared using a medium used in animal cell culture as a basal medium. Examples of basal media include IMDM medium, Medium 199, Eagle's Minimum Essential Medium (EMEM), aMEM medium, Dulbecco's modified Eagle's Medium (DMEM), Ham's F12 medium, RPMI 1640 medium, Fischer's medium, Neurobasal medium (Life Technologies Corporation), and mixtures of these. The medium may contain serum, or may be serum free. The medium may contain one or more substances such as albumin, insulin, transferrin, selenium, fatty acids, trace elements, 2-mercaptoethanol, thiol glycerol, lipids, amino acids, L-glutamine, non-essential amino acids, vitamins, growth factors, low-molecular-weight compounds, antibiotics, antioxidants, pyruvic acid, buffers, inorganic salts, cytokines and the like as necessary. Cytokines are proteins that promote blood cell differentiation, such as VEGF, TPO, SCF and the like. A preferred medium in the present invention is IMDM medium containing serum, insulin, transferrin, serine, thiol glycerol, ascorbic acid and TPO. More preferably, it also contains SCF. Moreover, when using an expression vector comprising a drug-responsive promoter such as a Tet-on® or Tet-off® system, the corresponding drug, such as tetracycline or doxycycline, is preferably contained in the medium in the overexpression step.

The culture conditions are not particularly limited, but for example the cells may be cultured in the presence of TPO (10 to 200 ng/mL, preferably about 50 to 100 ng/mL), in the presence of TPO (10 to 200 ng/mL, preferably about 50 to 100 ng/mL) and SCF (10 to 200 ng/mL, preferably about 50 ng/mL), or in the presence of TPO (10 to 200 ng/mL, preferably about 50 to 100 ng/mL), SCF (10 to 200 ng/mL, preferably about 50 ng/mL) and heparin (10 to 100 U/mL, preferably about 25 U/mL). For the culture temperature, culture at a temperature of 35.0° C. or more has been confirmed to promote differentiation of megakaryocytes or megakaryocyte precursor cells. The culture temperature is a temperature that does not damage the cells, such as preferably 35.0° C. to 42.0° C., or more preferably 36.0° C. to 40.0° C., or still more preferably 37.0° C. to 39.0° C.

A person skilled in the art can set the culture time appropriately by monitoring the number of megakaryocytes or megakaryocyte precursor cells and the like. For example, the proportion of megakaryocyte cells in a culture can be determined by using flow cytometry to analyze cell surface markers that are expressed specifically in megakaryocytes, and cells can then be cultured so that the proportion of megakaryocytes or megakaryocyte precursor cells, and of megakaryocytes in particular, is at least 50% or, for example, at least 60%, or 70%, or 80%, or 90% of the total cells in the culture. The number of days is not particularly limited as long as the desired megakaryocyte precursor cells are obtained, but is preferably at least 3 days, or more preferably at least 6 days, or still more preferably at least 9 days. Since a long culture time is not considered a particular problem, it may also be at least 12 days, or at least 18 days, or at least 24 days, or at least 30 days, or at least 42 days, or at least 48 days, or at least 54 days, or at least 60 days. Preferably the cells are also passaged as necessary during the culture period.

When transforming cells with a drug resistance gene, a drug such as puromycin, neomycin, kanamycin, chloramphenicol, erythromycin, tetracycline, hygromycin, ampicillin, Zeocin, blasticidin S, histidinol or the like may be used.

Techniques known to those skilled in the art in the production of megakaryocytes can be applied to the producing method of the present invention as long as they do not detract from the effects of the invention. For example, in one embodiment of the megakaryocyte producing method of the present invention, an (a) substance that inhibits the expression or function of a p53 gene product, (b) actomyosin complex function inhibitor, (c) ROCK inhibitor and (d) HDAC inhibitor may also be included in the medium. These methods may conform to the methods described in WO 2012/157586 for example.

Megakaryocyte cell production can also be increased by overexpressing an exogenous gene such as a c-MYC gene or other cancer gene or a polycomb gene as described in WO 2011/034073. In such an embodiment, the producing method of the invention of this application may also include a step of turning off overexpression in the megakaryocytes or megakaryocyte precursor cells and then culturing the cells. When overexpression is achieved with a drug-responsive vector for example, overexpression can be turned off by eliminating contact between the corresponding drug and the cells. When a vector containing LoxP is used, it can also be turned off by introducing Cre recombinase into the cells. When a transient expression vector is introduced together with RNA or a protein, it can be turned off by ending contact with the vector and the like. The medium used in this step may be the same as the medium used above.

The conditions for turning off overexpression and culturing the cells are not particularly limited, but a temperature of 35.0° C. to 42.0° C. is preferred, 36.0° C. to 40.0° C. is more preferred, and 37.0° C. to 39.0° C. is even more preferred.

The culture period after overexpression is turned off may be determined appropriately while monitoring the cell numbers and especially the number of megakaryocyte cells, but preferably it is at least 2 days, such as 2 to 14 days after overexpression is turned off. A culture period of 3 to 12 days is more preferred, and 4 to 10 days is even more preferred. Medium exchange or passaging is preferably performed appropriately during the culture period.

When sufficiently matured, the megakaryocytes obtained by the present invention can efficiently produce functional platelets. In this Description, megakaryocyte maturation means that the megakaryocytes have undergone sufficient multinucleation to be able to produce functional platelets. Megakaryocyte maturation can also be confirmed based on increased expression of megakaryocyte maturation-associated gene groups such as GATA1, p45 NF-E2 and beta1-tubulin, on proplatelet formation, and on multinucleation within the cells for example. These platelets have already been confirmed in vivo and in vitro to have strong thrombogenicity.

Moreover, megakaryocytes and/or megakaryocyte precursor cells can produce functional platelets even after cryopreservation and thawing. A megakaryocyte cell strain produced in the present invention can be distributed in a cryopreserved state.

(Method for Producing Platelets)

The platelet producing method of the present invention features the use of a culture produced by the method described above. In a more specific embodiment, the platelet producing method of the present invention includes a step of culturing the megakaryocytes, megakaryocyte precursor cells and/or megakaryocyte cell line obtained by the methods described above, and recovering platelets from the culture.

The culture conditions are not limited, but for example the cells may be cultured in the presence of TPO (10 to 200 ng/mL, preferably about 50 to 100 ng/mL), or in the presence of TPO (10 to 200 ng/mL, preferably about 50 to 100 ng/mL), SCF (10 to 200 ng/mL, preferably about 50 ng/mL) and heparin (10 to 100 U/mL, preferably about 25 U/mL).

The culture period is preferably at least 3 days, but is not particularly limited as long as the functionality of the produced platelets is maintained. For example, the culture period is 3 days to 14 days. The culture period is preferably 4 days to 12 days, or more preferably 5 days to 10 days.

The culture temperature is not particularly limited, and is 35.0° C. to 42.0° C. for example. The culture temperature is preferably 36.0° C. to 40° C., or more preferably 37.0° C. to 39.0° C.

In the producing method of the present invention, the megakaryocyte culture step may be performed under serum-free and/or feeder cell-free conditions. This is preferably a method in which megakaryocytes produced according to the methods of the present invention are cultured in medium containing TPO. When no feeder cells are used, a conditioned medium may be used in one embodiment. The conditioned medium is not particularly limited, and may be prepared by a person skilled in the art by known methods, but for example it can be obtained by appropriately culturing feeder cells, and then removing the feeder cells from the culture with a filter.

In one embodiment of the platelet producing method of the present invention, a ROCK inhibitor and/or actomyosin complex function inhibitor is added to the medium. The ROCK inhibitor and actomyosin complex function inhibitor may be the same as those used in the multinucleated megakaryocyte producing method described above. Examples of ROCK inhibitors include Y27632, fasudil hydrochloride and H1152 dihydrochloride. Examples of actomyosin complex function inhibitors include myosin ATPase activity inhibitors and myosin light-chain kinase inhibitors, such as blebbistatin, ML-7 and ML-9. A ROCK inhibitor or actomyosin complex function inhibitor may be added by itself, or a ROCK inhibitor and actomyosin complex function inhibitor may be added together.

0.1 μM to 30.0 μM of the ROCK inhibitor and/or actomyosin complex function inhibitor may be added for example. The inhibitor concentration is preferably 0.5 μM to 25.0 μM, or more preferably 1.0 μM to 20.0 μM, or still more preferably 5.0 μM to 15.0 μM.

The culture time after addition of the ROCK inhibitor and/or actomyosin complex function inhibitor may be 1 to 15 days for example. The culture time is preferably 3 to 13 days, or more preferably 5 to 11 days, or still more preferably 6, 7, 8, 9 or 10 days. Further increases in the proportion of CD42b-positive platelets can be achieved by adding a ROCK inhibitor and/or actomyosin complex function inhibitor.

The platelets can be isolated from the medium by methods known to those skilled in the art. The platelets obtained by the present invention are very safe platelets that express no exogenous genes. The megakaryocytes provided by the present invention may express an exogenous apoptosis suppression gene or cancer gene for example, although this is not a particular limitation. In this case, expression of this exogenous gene is suppressed in the platelet production step.

The platelets obtained by the present invention may be administered to a patient as a preparation. Depending on the administration, the platelets obtained by the method of the present invention may be stored and formulated with human plasma, infusion solution, citrated saline, a solution based on glucose-supplemented Ringer's acetate solution, PAS (platelet additive solution) (Gulliksson, H. et al., Transfusion 32:435-440 (1992)) or the like for example. The storage period is about 14 days beginning immediately after formulation, or preferably 10 days, or more preferably 8 days. The storage conditions are preferably room temperature (20° C. to 24° C.) with shaking agitation.

(Method for Transplanting or Transfusing Platelets)

The method for transplanting or transfusing the platelets of the present invention includes a step of transplanting or transfusing platelets produced by the method described above into a test subject. Platelets produced by the method of the present invention can be transfused by the same methods used to transfuse platelets obtained by ordinary methods, and can be administered appropriately to a test subject by a person skilled in the art.

As used in this Description, the term "test subject" refers to any vertebrates including mammals (such as cows, pigs, camels, llamas, horses, goats, rabbits, sheep, hamsters, guinea pigs, cats, dogs, rats and mice, non-human primates (such as crab-eating macaques, rhesus macaques, chimpanzees, and other monkeys) and humans) requiring transplantation or the like of platelets. Depending on the embodiment, the test subject may be a human or a non-human animal.

The present invention is explained in more detail below using examples, but the present invention is in no way limited by the examples.

EXAMPLES

Cells, Animals

A human ES KhES3 cell line provided by Dr. Hirofumi Suemori of Kyoto University and a human ES H1 cell line provided by Dr. Tatsutoshi Nakahata of Kyoto University were used. The ICR mice used in the experiments were purchased from Japan SLC, Inc. The animal experiments were performed according to the protocols of the University of Tokyo and Kyoto University. We took a prescribed seminar on the use of human ES cells, and used them according to the University of Tokyo's use plan, "Induction of hematopoietic stem cells and differentiated blood cells from human embryonic stem cells", and the use plan of the Kyoto University Center for iPS Cell Research and Application, "Studies on blood cell/neuronal differentiation from human ES cells".

Gelatin Coat 2 mL/dish of gelatin solution was added to each 60 mm dish and 4 mL/dish to each 100 mm dish, which was then shaken to distribute the solution overall, and incubated for at least 1 hour at 37° C. to coat the dish.

Matrigel Coat

The 6-well plates, 60-mm dishes and pipettes to be coated were first cooled to 4° C. A 50× diluted Matrigel solution that had been stored at 4° C. was added while still cool in the amount of 2 mL/well per 6-well plate and 3 mL/dish per 60-mm dish, and incubated for at least 1 hour at 37° C. to obtain coatings.

Establishment of Mouse Embryonic Fibroblasts (MEF)

Mouse embryonic fibroblasts were established using ICR mouse E12.5 embryos. A 12-day pregnant mouse was euthanized, the uterus was removed aseptically, and the embryos were separated manually from the placenta and the like. After manual removal of the heads and abdominal organs, these were minced finely with scissors. 1 mL of 0.05% trypsin EDTA was added per mouse, and the mixture was placed in a cell culture flask and stirred for 20 minutes at 300 rpm with a magnetic stirrer at room temperature to isolate cells. 2× the amount of MEF medium was added to stop the reaction, and the sample was transferred to a 50 mL centrifuge tube and centrifuged at 400 g for 10 minutes, after which the supernatant was removed. The pellet was suspended in 10 mL of DMEM+10% FBS+L-glutamine medium per embryo, and the cells of one embryo were seeded on a 100 mm dish and incubated at 37.0° C. in 10% $CO_2$ (day 0). The medium was completely exchanged on day 1. On day 2 the cells were detached with 0.05% trypsin EDTA and collected, and passaged and expansion cultured at a calculation of one 100-mm dish to 1.2 150-mm dishes. On day 4 the cells were collected and cryopreserved at −80° C. with a TC protector at $4 \times 10^6$ cells/tube.

The procedures for using the MEFs in iPS cell culture were as follows. The frozen tube was thawed, and the contents of one tube were seeded on one 100-mm dish. The day after thawing, a 1 mg/mL MMC solution was added to a final concentration of 10 mg/mL, and incubated for 2 hours at 37° C. to inactivate cell division. The cells were collected with 0.05% trypsin EDTA, and $3 \times 10^5$ cells were seeded on a previously gelatin coated 60-mm dish, and used on the following day and subsequently.

C3H10T1/2 Cell Culture

C3H10T1/2 cells were diluted, maintained and passaged so as to expand them from 1 dish to 8 to 10 dishes at subconfluence. Passage was performed every 3 to 4 days, and medium exchange every other day.

At the time of use, 1 mg/mL MMC solution was added to the subconfluent cell dish to a final concentration of 10 mg/mL, and incubated for 2 hours at 37° C. to inactivate cell division. The cells were collected with 0.05% trypsin EDTA, and $8 \times 10^5$ cells were seeded on a previously gelatin coated 100-mm dish, and used on the following day or subsequently.

OP9-DL1 Cell Culture

OP9-DL1 cells were diluted, maintained and passages so as to expand them from 1 dish to 8 to 10 dishes at subconfluence. Passage was performed every 3 to 4 days, and medium exchange every other day. At the time of use, the cells were seeded and further cultured on a gelatin-coated 6-well plate, and used when they reached confluence.

hPSC Maintenance Culture Using MEFs

KSR medium was used, and the medium was exchanged every day during culture. Passage was performed using TK solution. The culture supernatant was aspirated, 1 mL/dish of TK solution was added, and the cells were incubated for 5 minutes at 37° C. The supernatant was aspirated, and 3 to 4 mL of KSR medium were added. The colonies were somewhat detached from the bottom of the dish by tapping. The colonies were finely crushed to a certain degree by pipetting with a Pipetman (p1000), and the necessary quantity was seeded on a dish seeded with new MEFs. The day after passage the medium was exchanged, and was subsequently exchanged every day.

hPSC Maintenance Culture Using Matrigel

StemFit medium was used. The medium was exchanged every other day. The cells were washed twice with PBS at the time of passage, 1 mL/dish of TrypLE select was added and reacted for 3 minutes at 37° C., and the cells were pipetted with a p1000 Pipetman and collected in a 15 mL centrifuge tube. The reaction was stopped with MEF medium, and following centrifugation and supernatant removal, 1 to 2 mL of StemFit was added to suspend the cells, which were then counted. During seeding, the cells were passaged at a rate of $3 \times 10^4$ to $1 \times 10^5$ cells per 60-mm dish, and 10 mM of Y27632 was added to the medium to prevent cell death.

The day after passage the medium was replaced with StemFit medium, and was then replaced every other day thereafter.

Blood Cell Differentiation from hPSC Using C3H10T1/2

Human ES cells that had been maintenance cultured in MEF were detached from the bottom of the dish in colony form as at the time of passage, and seeded on an inactivated C3H10T1/2 dish that had been prepared the previous day. The seeding rate was roughly $5 \times 10^4$ to $2 \times 10^5$ cells per 10-cm dish, although this is an estimate because the cells could not be counted. The medium was blood cell differentiation medium to which VEGF had been added to a final concentration of 20 ng/mL. Single cells were collected using 0.05% trypsin EDTA as necessary, the cells were counted, Y27632 was added to 10 mM, and the cells were differentiated as single cells.

The medium was exchanged on day 3, day 6, day 9, day 11 and day 13 after differentiation.

When analyzing cells during differentiation, the culture supernatant was removed, the cells were washed twice with PBS, and 2 mL/dish of 0.25% trypsin EDTA was added and incubated for 5 minutes at 37° C. The cells were separated into single cells by pipetting with a Pipetman (p1000), and collected in a 15 mL centrifuge tube. Blood cell differentiation medium was added to stop the reaction, and after centrifugation and removal of the supernatant, the cells were suspended in the necessary medium and analyzed.

Method for Differentiating Hematopoietic Mesoderm from hPSC in Serum-Free, Feeder-Free System hPSC cells that had been maintenance cultured in Matrigel were collected by detaching single cells from the dish as at the time of passage, and seeded on Matrigel-coated 60-mm dishes. For the medium, 50 ng/mL of Activin A, 50 ng/mL of BMP4, 3 mM of CHIR99021, 125 ng/mL of NOGGIN, 100 ng/mL of DKK-1 and 2.5 mM of XAV939 were added as necessary to CDM or StemFit medium, and on day 2 the medium was replaced with the same composition. 10 mM of Y27632 was added to suppress cell death on days 0 to 2 only.

The cells were collected on day 4 and washed twice with PBS, after which 1 mL/dish of TrypLE select was added and reacted for 3 minutes at 37° C. The cells were detached by pipetting with a Pipetman (p1000), and collected in a 15 mL centrifuge tube. Blood cell differentiation medium was added to stop the reaction, and following centrifugation and removal of the supernatant, the cells were suspended in blood cell differentiation medium, and counted. These cells were then differentiated into blood cells by the following two methods.

Feeder-Free Blood Cell Differentiation Via Spheroid Formation

Cells collected on day 4 were seeded $2\times10^6$ cells per 100-mm EZSPHERE dish (AGC Techno Glass Co., Ltd.). Blood cell differentiation medium to which 50 ng/mL of VEGF, 50 ng/mL of bFGF, 10 mM of SB431542 and 10 units/mL of heparin had been added was used. Spheroids that had formed by day 7 were collected by pipetting in a centrifuge tube, and following centrifugation and removal of the supernatant, these were suspended in blood cell differentiation medium and passaged on PrimeSurface 90-mm dishes (Sumitomo Bakelite Co., Ltd.) at an expansion rate of 1 to 3 dishes from 1 dish. 50 ng/mL of VEGF, 50 ng/mL of bFGF and 10 units/mL of heparin were added to the medium. The medium was subsequently replaced with the same composition on days 10 and 12. On day 14, all the cells in the plate were stirred by pipetting, passed through a 40 mm cell strainer, and collected in a 50 mL centrifuge tube. Following centrifugation the supernatant was removed, and the cells were suspended in blood cell differentiation medium, and counted.

Feeder-Free Blood Cell Differentiation Using Cell Sorter

Cells collected on day 4 were reacted with antibodies, and directly sorted $3\times10^4$ cells/well on Matrigel-coated 6-well plates using a FACSAria II cell sorter. The Matrigel solution was removed from the wells, and 2 mL/well of blood cell differentiation medium+50 ng/mL VEGF, 50 ng/mL bFGF, 10 mM SB431542, 10 units/mL heparin+10 mM Y27632 was added in advance.

On day 7, day 10 and day 12, the medium was replaced with blood cell differentiation medium to which 50 ng/mL of VEGF, 50 ng/mL of bFGF and 10 units/mL of heparin had been added. On day 14, the supernatant was collected in a 15 mL centrifuge tube, washed twice with PBS, and then collected in the same centrifuge tube, 1 mL/well of trypsLE select was added and reacted for 5 minutes at 37° C., and the cells were detached from the bottom by pipetting with a Pipetman (p1000) and collected in the same centrifuge tube in the form of single cells. After centrifugation and removal of the supernatant, the cells were suspended in blood cell differentiation medium, and used in subsequent analysis.

Induction of Megakaryocytes, Erythroblasts and T-Cells from Resulting Blood Cells Induced blood cells from day 14 were induced to differentiate into different kinds of blood cells. For megakaryocyte induction, the blood cells were seeded $1\times10^5$ cells/well on 6-well plates seeded with C3H10T1/2 cells. The medium was blood cell differentiation medium to which 50 ng/mL of SCF and 50 ng/mL of TPO had been added. After 7 days of culture the cells were collected and analyzed by flow cytometry.

For erythroblast induction, the blood cells were seeded $1\times10^5$ cells/well on 6-well plates seeded with C3H10T1/2 cells. The medium was blood cell differentiation medium to which 50 ng/mL of SCF and 3 units/mL of EPO had been added. After 7 days of culture the cells were collected and analyzed by flow cytometry.

For T-cell induction, the blood cells were seeded $1\times10^5$-6 cells/well on 6-well plates on which OP9-DL1 cells had been seeded and made confluent. The medium was OP9 medium to which 10 ng/mL of SCF, 5 ng/mL of FLT3 Ligand and 5 ng/mL of IL-7 had been added. After 14 days of culture the cells were collected and analyzed by flow cytometry.

Colony Forming Ability Assay

Colony forming ability was measured using blood cells from day 14 of induction. $5\times10^4$ to $1\times10^5$ blood cells were mixed with 4 mL of Methocult H4434 classic, seeded on a 60-mm dish, and then cultured for 14 days at 37° C. in a 5% 002 environment, and the formed colonies were observed under a microscope.

Flow Cytometry

Cells in a single-cell state were prepared as necessary, and fluorescent labeled antibodies were also included as necessary in amounts matching the cell numbers. After addition of the necessary amounts of the antibodies, the cells were incubated and reacted for at least 30 minutes at 4° C. These were then diluted with SM and centrifuged, the supernatant was removed, and the cells were suspended in the necessary amount of SMPI and analyzed. When feeder cells were mixed in with the hPSC-derived cells, these were separated by FSC vs SSC gating and by means of the GFP expressed in the hPSC cells.

qRT-PCR

RNA was collected from the target cells using RNeasy or miRNeasy (Qiagen GmbH) according to the manual. cDNA was synthesized from the RNA using PrimeScript2 (Takara Bio Inc.) or ReverTraAce (Toyobo Co., Ltd.) according to the manual.

In qRT-PCR, the reaction solution was prepared as follows using Roche MasterMix and Universal probe.

| | |
|---|---|
| 2x MasterMix | 10 mL/sample |
| Probe (10 mM) | 0.4 mL/sample |
| Fwd Primer (10 mM) | 0.4 mL/sample |
| Rev Primer (10 mM) | 0.4 mL/sample |
| Template cDNA | 1 mL/sample |
| $H_2O$ | 7.8 mL/sample |
| Total | 20 mL/sample |

StepOnePlus was used for the reaction and data collection. The reaction program was as follows.

| | |
|---|---|
| First step (1 cycle) | 95° C., 10 min |
| Second step (40 cycles) | 95° C., 10 sec |
| | 60° C., 30 sec |

The primers are listed below. The primers were designed using the Assay design center of the Roche Universal Primer website: (https://lifescience.roche.com/webapp/wcs/stores/servlet/CategoryDisplay?tab=Assay+Design+Center&identifier=Universal+Probe+Library&langld=-1).

TABLE 1

| Gene | Universal Probe No. | Fwd | Rev |
| --- | --- | --- | --- |
| Beta-actin (ACTB) | 27 | tcctccctggagaagagcta (SEQ ID NO: 1) | cgtggatgccacaggact (SEQ ID NO: 2) |
| NANOG | 69 | atgcctcacacggagactgt (SEQ ID NO: 3) | cagggctgtcctgaataagc (SEQ ID NO: 4) |
| OCT3/4 (POU5F1) | 69 | gcttcaagaacatgtgtaagctg (SEQ ID NO: 5) | cacgagggtttctgctttg (SEQ ID NO: 6) |
| T | 23 | gctgtgacaggtacccaacc (SEQ ID NO: 7) | catgcaggtgagttgtcagaa (SEQ ID NO: 8) |
| APJ | 79 | ggcagttctttgggtgct (SEQ ID NO: 9) | gtggtgcgtaacaccatgac (SEQ ID NO: 10) |
| ETV2 | 6 | gggtgcatggtatgaaatgg (SEQ ID NO: 11) | aaggccttctgaatgttctctg (SEQ ID NO: 12) |
| KDR | 18 | gaacatttgggaaatctcttgc (SEQ ID NO: 13) | cggaagaacaatgtagtctttgc (SEQ ID NO: 14) |
| RUNX1 | 21 | acaaacccaccgcaagtc (SEQ ID NO: 15) | catctagtttctgccgatgtctt (SEQ ID NO: 16) |

Gene Expression Array Analysis

A GeneChip made by Affymetrix was used. GeneSpring 13.0 was used for analysis. Sample RNA was analyzed using a GeneChip® WT PLUS Reagent Kit. The samples were prepared according to the manual. DAVID was used for gene ontology analysis.

Results

Blood Cell Differentiation System from hPSC can be Traced Step by Step Using Cell Surface Markers The process of differentiation of blood cells from hPSC cells is thought to progress from mesoderm through hemangioblasts to blood cells. Using methods reported previously (Takayama, N. et al., Blood 111, 5298-5306 (2008)), the human ES cell strain KhES3 was used to investigate whether cell surface markers can be used to trace this process.

A co-culture system with C3H10T1/2 cells was analyzed over time from the start of co-culture (day 0) to the appearance of blood cells (day 12) to trace changes in hPSC cell surface markers. All of the cells in the culture were collected, and expression of cell surface antigens was investigated by flow cytometry. The analyzed surface antigens were selected with reference to previous reports (Evseenko, D. et al., P Natl Acad Sci USA 107, 13742-13747 (2010); Vodyanik, M. A. et al., Cell Stem Cell 7, 718-729 (2010); Vodyanik, M. A. et al., Blood 108, 2095-2105 (2006)). FIG. 2A shows an outline of the experiment, and the results are shown in FIGS. 2B to 2D.

A new cell population could be confirmed on day 3 after the start of co-culture. This cell population was characterized by being CD56+APJ+.

Day 5 saw the first appearance of cells positive for CD34, which is known as a hemangioblast marker, and the proportion of this cell population increased on days 6 and 7. Cells positive for CD43, which is known as an early blood cell marker, appeared for the first time on day 8 and subsequent days. This cell population continued to increase from day 12 on.

These results show that CD56+APJ+ cells appear first on days 0 to 4, CD34+ cells on days 5 to 7, and CD43+ cells from day 8 on. This time line is extremely stable, and was confirmed with good reproducibility.

These results shown that the differentiation process is composed of four cell states with three steps between them. That is, the four cell states are hPSC, CD56+APJ+ cells, CD34+ cells and CD43+ cells. The steps between this were called the initial step (days 0 to 4), intermediate step (days 4 to 7) and late step (day 7 or more days).

Figure 1:
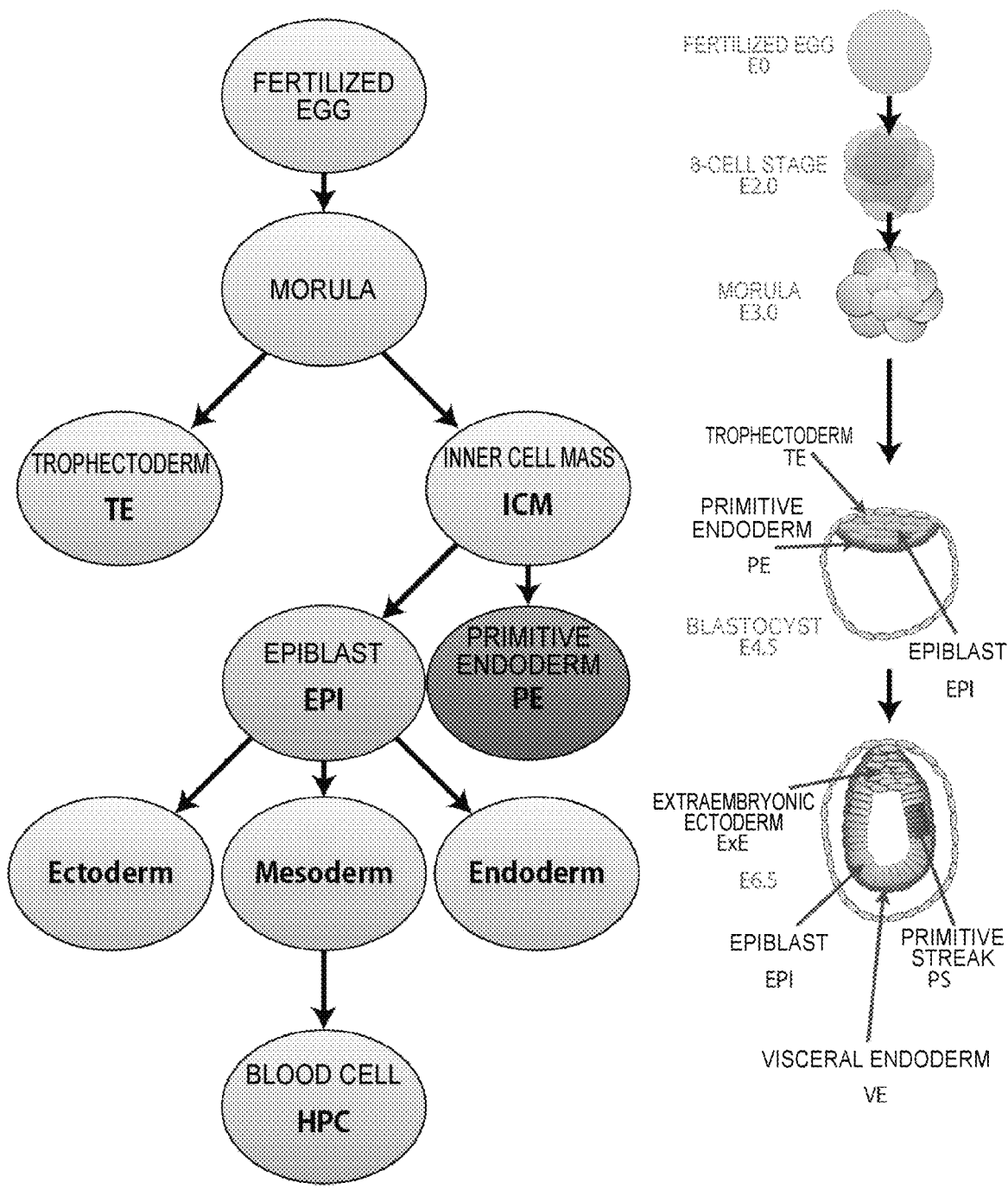
FIG. 1 shows a blood cell development lineage in mice. A hierarchical map of the development lineage is shown at left as a tree diagram, while an outline of the embryonic structures at the corresponding stages is shown at right.

To confirm what cells actually constituted each cell population, the cells were sorted and collected by FACS, and gene expression was confirmed by quantitative PCR. The results are shown in FIG. 1E. The pluripotent stem cell markers NANOG and OCT3/4 were highly expressed only in the hPSC cells, while the characteristic mesoderm genes T (Brachyury) and APJ were only common in the CD56+APJ+ cells identified on day 4, and ETV2 and KDR, which are important for hemangioblasts, were only common in the CD34+ cells identified on day 7. The gene RUNX1, which is known as an essential gene for blood cell development, increased in the CD56+APJ+ cell population from day 4, and was further increased in the CD34+ cells on day 7. These results suggest that the various cell populations identified in the differentiation process match the respective stages recognized in the development process (mesoderm, hemangioblasts, blood cells), and show that surface markers can be used to trace the differentiation process. They also suggest strongly that the RUNX1-positive CD56+APJ+ cells on day 4 are blood cell-producing mesoderm.

Intermediate and Later Steps of Existing Blood Cell Differentiation Systems could be Improved To investigate whether satisfactory differentiation induction efficiency is being obtained with existing systems, the proportions of CD56+APJ+ cells on day 4 and CD43+ cells on day 10 were measured as a percentage of all differentiated cells. As a result, CD56+APJ+ cells could already be differentiated at a rate of about 20% to 40% in the initial step (FIG. 3A, B). This suggests that satisfactory mesoderm induction can be obtained with only a co-culture of feeder cells. However, the proportion of CD43+ cells only reaches a few percent, a very low level of efficiency (FIGS. 3C, D). This suggests that blood cells are not adequately induced from mesoderm in the intermediate and later steps. To achieve the object of the invention, the rate of blood cell differentiation induction from mesoderm needs to be somewhat higher, and there appears to be room for improvement.

Three Signals Play an Important Role in the Initial Step, but Differ in Importance Next, the important signal factors that function at each stage were investigated individually. The initial step was investigated first.

Figure 4:
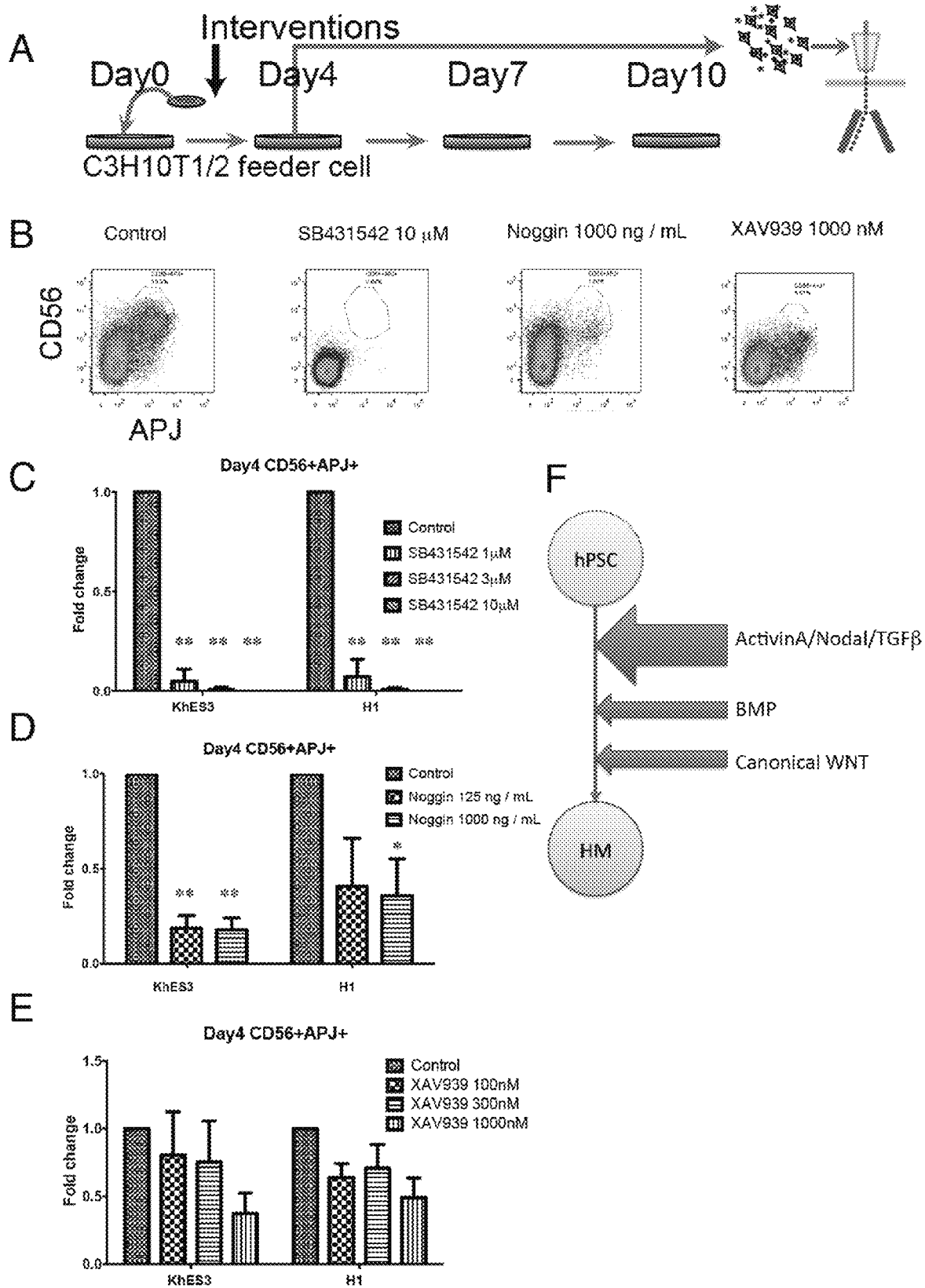
FIG. 4A shows an outline of an experiment in which three important signal factors were identified by interventions in the initial step. The intervention factor was added on days 0 to 4, and the percentage occurrence of mesodermal cells was analyzed on day 4.
FIG. 4B shows the occurrence pattern of CD56+APJ+ cells on day 4 with each factor added.
FIG. 4C shows the effects of SB431542 (TGFβ inhibitor) in comparison with a control group. The results show average plus standard deviation. A significant decrease in the mesodermal cell population was confirmed from addition of SB431542 (n=3, **p<0.01, paired t-test), beginning at a low concentration.
FIG. 4D shows the effects of NOGGIN (BMP antagonist) in comparison with a control group. The results show average plus standard deviation. A decrease in the mesodermal cell population was confirmed due to addition of NOGGIN (n=3, *p<0.05, **p<0.01, paired t-test).
FIG. 4E shows the effects of XAV939 (canonical WNT signal inhibitor) in comparison with control group. The results show average plus standard deviation. The mesodermal cell population tended to decrease when XAV939 was added, although the results were not statistically significant (n=3, paired t-test).
FIG. 4F shows that there were differences in the effectiveness of each, with TGFβ having the greatest effect. The size of the arrow indicates the degree of effect.

Taking cell surface markers as an evaluation standard, KhES3 and H1 cells were used to investigate what changes are seen in the occurrence of CD56+APJ+ cells due to interventions in the initial step. Because the system uses C3H10T1/2 cells and serum and is affected by multiple unknown substances, in this study it was necessary to add inhibitors and antagonists to three factors (Nodal/Activin A/TGFβ, BMP4, canonical WNT signal) that are considered important for mesoderm induction in the development process in order to investigate whether the three signals play an important role. FIG. 4A shows an outline of the experiment. For the added concentrations of each factor, the maximum concentration was determined with reference to previous reports, and this was then diluted to investigate concentration (Inman, G. J. et al., Mol. Pharmacol. 62, 65-74 (2002); Xu, R.-H. et al., Nat Meth 2, 185-190 (2005); Huang, S.-M. A. et al., Nature 461, 614-620 (2009)).

FIG. 4B shows FACS plots of the occurrence patterns of CD56+APJ+ cells on day 4 of KhES3 differentiation with each factor added.

First, the Nodal/Activin A/TGFβ inhibitor SB431542 was added to investigate the importance of the TGFβ signal in the initial step. The results are shown in FIG. 4C. It was possible to confirm a sharp drop in the ratio of CD56+APJ+ cells at the low concentration point. The effect is extremely strong, suggesting that the TGFβ signal is an essential factor in the initial step.

Next, the physiological BMP antagonist NOGGIN was added to confirm the effect of BMP4. The results are shown in FIG. 4D. A drop in CD56+APJ+ cells was confirmed, but the effect was limited, and the cells were not eliminated even at higher concentrations.

Finally, to confirm the effect of the canonical WNT signal, we added XAV939, which is a stabilizer of the canonical WNT pathway inhibiting factor AXIN. This inhibits the canonical WNT signal by accelerating b-catenin decomposition. The results are shown in FIG. 4E. A reduction in CD56+APJ+ cells was confirmed as a result. As in the case of BMP, this effect was limited, and the cells were not eliminated even at higher concentrations.

These results shown that three different signals that have been identified as mesoderm induction factors in developmental biology, namely the Nodal/Activin A/TGFβ signal, BMP signal and canonical WNT signal, each affected the differentiation induction process in the course of mesoderm development from hPSC cells. The degree of this effect varied, and while the Nodal/Activin A/TGFβ signal was an essential factor, the BMP4 and canonical WNT signals were associated with mesoderm induction but their effects were limited. FIG. 4F gives an outline of the results. The size of the arrow represents the effectiveness of the signal.

Blood Cell Differentiation Efficiency is Greatly Improved by Improving the Intermediate Step The intermediate step was investigated next. In existing systems, the CD43+ cell occurrence rate on day 10 has been a low rate of less than 1% (FIG. 3C, D). A low blood cell induction efficiency is not convenient for evaluating the blood cell productivity of mesoderm. Specifically, there is a risk that both cells with high productivity and cells with low productivity may be evaluated as having low productivity if the blood cell induction efficiency is low.

We therefore performed tests with KhES3 and H1 cells with the aim of further improving blood cell induction efficiency by improving the culture conditions (external factors) in the intermediate stage.

Figure 5:
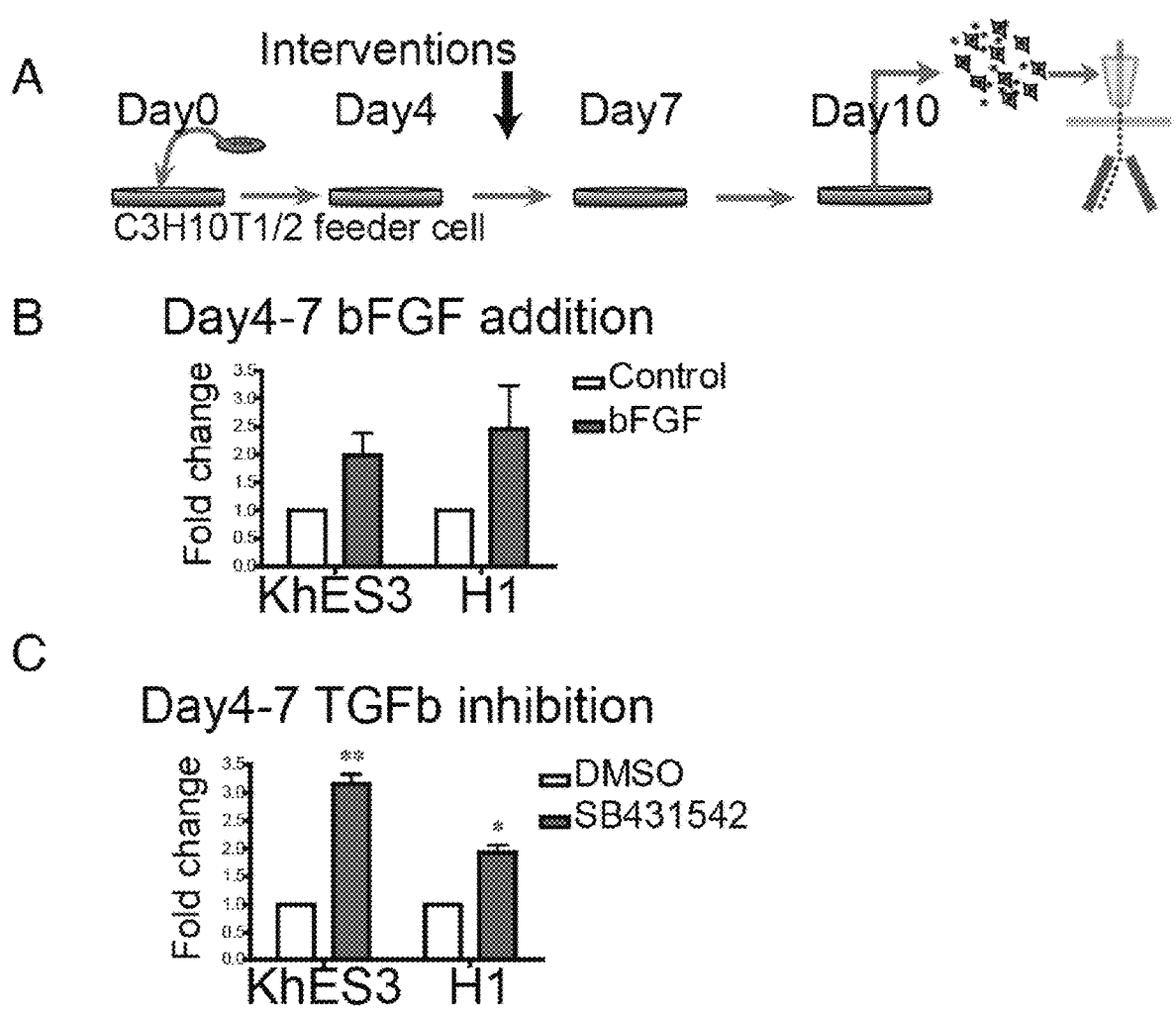
FIG. 5A shows an outline of an experiment showing that improved differentiation was obtained due to addition of two factors in the intermediate step. Each factor was added in the intermediate step on days 4 to 7, and the percentage occurrence of blood cells on day 10 was analyzed.
FIG. 5B shows the effects of bFGF addition in comparison with a control group. The percentage occurrence of blood cells on day 10 tended to be better when bFGF was added, although the difference was not statistically significant. The results show average plus standard deviation (n=3, paired t-test).
FIG. 5C shows the effects of SB431542 addition in comparison with a DMSO group. The percentage occurrence of blood cells on day 10 was significantly improved due to addition of SB431542. The results show average plus standard deviation (n=3, *p<0.05, **p<0.01, paired t-test).

In this step, molecules that might promote blood cell induction and inhibitors of molecules that might inhibit blood cell induction were added in the presence of VEGF, which is used in existing protocols. FIG. 5A shows an outline of the experiment.

bFGF has been reported as an essential molecule for hemangioblast induction. bFGF is essential for BL-CFC induction. Therefore, bFGF was added to this system, and heparin was also added to enhance the effect because it has a stabilizing effect on bFGF. The results are shown in FIG. 5B. Blood cell production efficiency on day 10 was increased by addition of bFGF and heparin.

Because blood cell production efficiency is reported to increase when the TGFβ signal is blocked, the inhibitor SB431542 was added at this point. The results are shown in FIG. 5C. In accordance with existing reports, blood cell production efficiency had increased by day 10.

Blood Cell Differentiation Ability could be Evaluated More Exactly when Mesoderm was Purified Having identified multiple important factors in the initial step and intermediate step, we were prepared to set up a system for evaluating the blood cell differentiation potential of mesoderm. However, from the analysis thus far it appeared that on day 4 nearly half of the cells were not CD56+APJ+ cells, and that these subsequently persisted in the culture environment, suggesting that blood cell differentiation might be affected by other factors such as the paracrine effect. The proportion of CD56+APJ+ cells varied among trials (FIG. 7D), so it seemed necessary to exclude the possibility of other effects.

Figure 7:
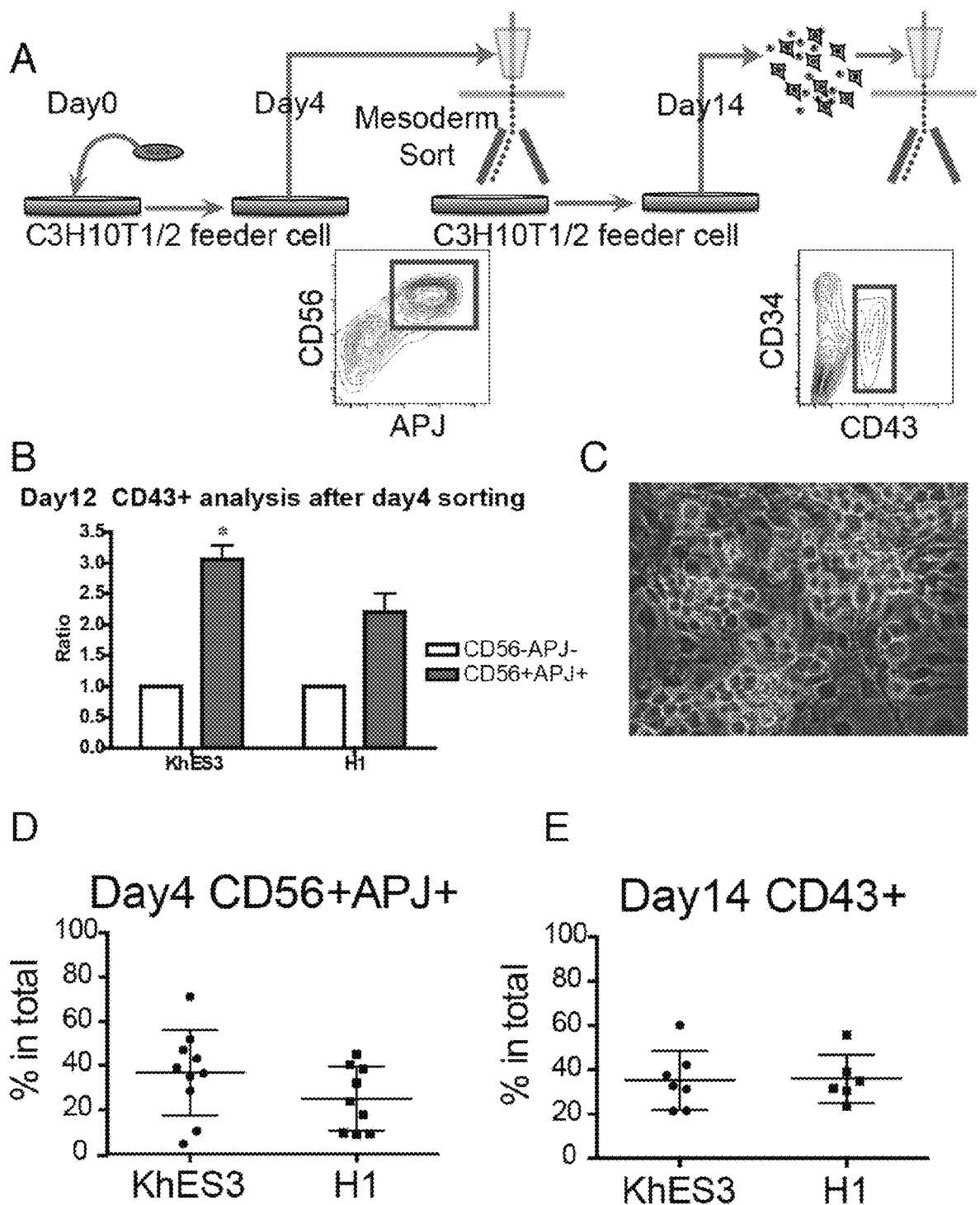
FIG. 7A shows an outline of an experiment in which stable blood cell differentiation was achieved by purifying mesoderm. Only the CD56+APJ+ mesodermal cells were sorted on day 4, and seeded on a new feeder. This was cultured continuously, and the blood cells were analyzed on day 14.
FIG. 7B shows that the day 4 CD56+APJ+ cells differentiated into blood cells more efficiently than the CD56−APJ− cells. The results show average plus standard deviation (n=3, *p<0.05, paired t-test).
FIG. 7C confirms the appearance of spherical cells in colonies on day 14.
FIG. 7D shows the percentage occurrence of CD56+APJ+ cells on day 4. The results are represented as dots, showing average plus standard deviation. There is at least 10% variation between trials.
FIG. 7E shows the percentage occurrence of CD43+ blood cells on day 14. The results are represented as dots, showing average plus standard deviation. Overall, 20% to 60% of the cells differentiated into blood cells, and it was possible to construct a highly efficient differentiation system.

Thus, in order to accurately evaluate the blood cell differentiation potential of the mesoderm itself, we tested whether blood cell induction could be performed with purified mesoderm. As shown in FIG. 7A, only those cells that had formed mesoderm by day 4 were purified by FACS, culture was continued under the stipulated conditions in a new culture dish, and production of blood cells in KhES3 and H1 cells was confirmed. The blood cell differentiation potential of CD56-APJ-cells was also evaluated in the same way at the same time.

The results are shown in FIG. 7B. The CD56+APJ+ cells were found to produce blood cells more efficiently than the CD56−APJ− cells. As shown in the photograph in FIG. 7C, it was confirmed that spherical cells appeared as colonies from the sorted cells. Cells having blood cell markers were also confirmed by FCM. The proportion of CD43+ cells as a percentage of the total differentiated cells is shown in FIG. 7E. The overall rate was 20%, rising to about 60% differentiated blood cells at the highest point. This shows that while blood cells are produced from a CD56+APJ+ cell population, no other cell population is necessary for producing those cells, and highly efficient induction of blood cell differentiation is possible with the present method.

Figure 8:
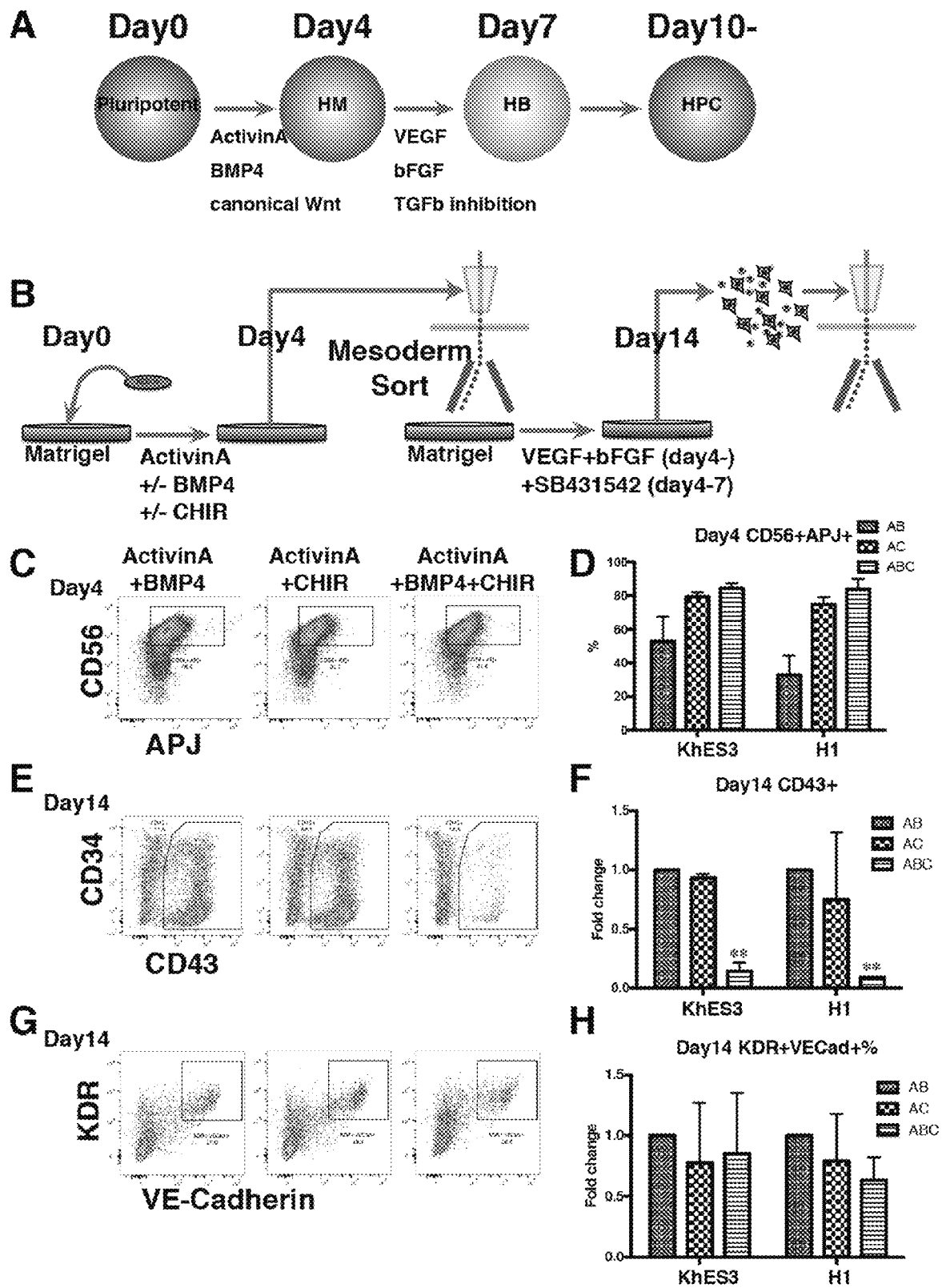
FIG. 8A illustrates the finding that there are multiple conditions under which hematopoietic mesodermal cells can be differentiated by performing the initial step in a serum-free, feeder-free system. The signal factors necessary for each step are shown.
FIG. 8B illustrates an outline of the experiment. Differentiation on days 0 to 4 was performed with a combination of Matrigel and three signal factors, on day 4 the cells were sorted and seeded on a new Matrigel-coated plate, culture was continued, and on day 14 all the cells were analyzed to evaluate blood cell differentiation efficiency. 50 ng/mL Activin A, 50 ng/mL BMP4 and 3 µM CHIR99021 were used as the factors.
FIG. 8C shows the occurrence pattern of CD56+APJ+ cells under each condition on day 4.
FIG. 8D is a bar graph showing the percentage occurrence of CD56+APJ+ cells under each condition. The cells occurred under each condition, and the AC and ABC conditions induced mesodermal cells most efficiently.
FIG. 8E shows the occurrence pattern of CD43+ cells on day 14.
FIG. 8F shows the percentage occurrence of CD43+ cells under each condition, represented as average plus standard deviation with AB as the standard. Blood cells were efficiently differentiated under conditions AB and AC, but under condition ABC the percentage of cells becoming blood cells was dramatically less (n=3, **p<0.01, paired t-test).
FIG. 8G shows the occurrence pattern of vascular endothelial cells (KDR+VE−Cadherin+ cells) on day 14.
FIG. 8H shows the percentage occurrence of KDR+VE−Cadherin+ cells under each condition, represented as average plus standard deviation with AB as the standard. No statistically significant difference was found among the conditions (n=3, paired t-test).

Hematopoietic Mesoderm Induction is Confirmed to Involve Multiple Pathways Rather than a Single Pathway Based on the results thus far, the necessary factors in each step are shown in FIG. 8A. It was shown that a mesoderm stage exists in the pathway from pluripotent stem cells to blood cells, that three factor groups seem to be necessary for inducing this mesoderm, and that a system was established for evaluating the blood cell production potential of mesoderm. By combining these, we were ready to examine the target pathway from pluripotent stem cells to blood cells, and in particular to investigate how mesoderm as a source of blood cells originates from pluripotent stem cells.

To regulate the signals more accurately, it seemed advisable to reduce unknown substances as much as possible. Feeder cells and serum are useful for cell survival and differentiation, but disadvantageous in terms of being unknown factors. Therefore, to find out what signals are important in the steps leading up to the initial mesoderm, we investigated whether differentiation in a serum-free, feeder-free environment was possible only in the initial step. FIG. 8B shows an outline of the experiment. When differentiation was attempted using serum-free medium and Matrigel, blood cell differentiation efficiency was confirmed to be high under these conditions, so the subsequent experiments were performed under serum-free, feeder-free conditions. From the intermediate step onwards, efficiency declined dramatically under serum-free conditions, so conditions using serum were still applied to evaluating blood cell production potential.

To then verify what induction conditions would yield mesoderm having blood cell differentiation potential, mesoderm induction was attempted using various combinations of three factors that are important in the initial step. Because the Nodal/Activin A/TGFβ signal appeared to be essential based on the results of FIG. 4, three protocols were attempted combining this with BMP4 and the canonical WNT signal. The experiment was performed using KhES3 and H1 cells.

CD56+APJ+ cells were confirmed under all conditions, and it appeared that mesoderm differentiation was achieved. The results are shown in FIG. 8C. CD56+APJ+ cells were efficiently induced with differences in induction rates among the various conditions, in the order of AB<AC≤ABC. The results are shown in FIG. 8D.

These cells were purified by FACS and cultured under blood cell differentiation conditions up to day 14, and blood cell induction efficiency was evaluated. The results are shown in FIGS. 8E and 8F. Surprisingly, blood cell induction efficiency was much lower under the ABC condition.

To confirm the properties of the mesoderm in more detail, vascular endothelial cell markers were also confirmed on day 14. The results are shown in FIGS. 8G and 8H. No great differences were found among the conditions.

Figure 9:
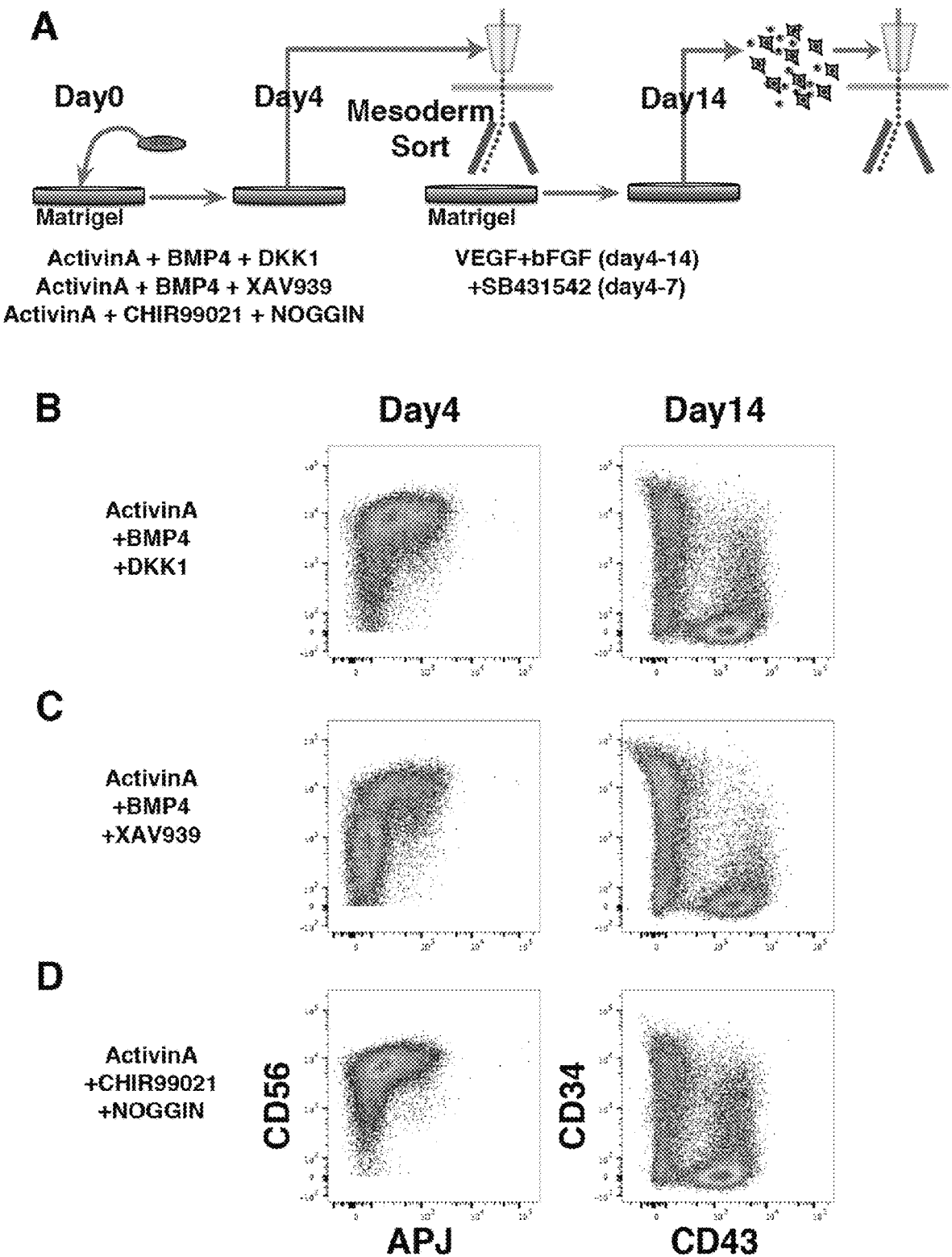
FIG. 9A shows an outline of an experiment showing that blood cell differentiation was unaffected even when one signal was blocked. The antagonist DKK1 (100 ng/mL) and the inhibitor XAV939 (2.5 µM) were added to block the canonical WNT signal under the AB condition (ABD and ABX condition), while the antagonist NOGGIN (125 ng/mL) was added to block the BMP signal under the AC condition (ACN condition). From day 4 onwards culture was continued under the same conditions for all. KhES3 was used as the cell strain.
FIG. 9B shows FACS plots on day 4 and day 14 of differentiation under the ABD condition.
FIG. 9C shows FACS plots on day 4 and day 14 of differentiation under the ABX condition.
FIG. 9D shows FACS plots on day 4 and day 14 of differentiation under the ACN condition. In all cases, a CD56+APJ+ cell population and CD43+ cell population were produced efficiently.

Because Activin A, BMP4 and WNT are thought to induce expression of each other, antagonists and inhibitors to each were added in order to show that there was really no interference under the AB and AC conditions. Indeed, highly efficient blood cell differentiation occurred under the conditions of Activin A+BMP4+XAV939 (AB with canonical WNT inhibition), Activin A+BMP4+DKK-1 (AB with WNT signal inhibition) and Activin A+CHIR99021+NOGGIN (AC with BMP4 signal inhibition) (FIG. 9).

These results show that blood cell-producing mesoderm can be differentiated with specific factors even under serum-free, feeder-free conditions. Moreover, the three factors that were important in the initial step induced mesoderm without blood cell differentiation potential when combined together, but could induce mesoderm with strong blood cell differentiation potential using two different combinations of two factors.

Differences in Gene Expression in Mesoderm and Blood Cells Under Different Conditions CD56+APJ+ cells induced under AB and AC conditions had blood cell differentiation potential, while CD56+APJ+ cells induced under ABC conditions lost that potential. To find the reason for this, we used KhES3 to investigate the gene expression patterns of the respective cells. RNA was collected from the differentiated cells, and analyzed with a gene expression array with the results shown in FIG. 10. FIG. 10A shows the results of a clustering analysis using gene groups that differed among the hPSC and AB, AC and ABC conditions on day 4. In comparison with the hPSC cells on day 0, the day 4 AB, AC and ABC cells exhibited extremely similar expression patterns. FIG. 10B is a Venn's diagram analyzing the common parts in the comparison. Looking in detail at the genes that were common to all the conditions, there was a decrease in the expression of a gene group associated with pluripotency in the day 4 cells, as well as a rise in the expression of a gene group characteristic of mesoderm, and a rise in the expression of genes associated with epithelial-mesenchymal transition (EMT) was also confirmed. This showed that the day 4 CD56+APJ+ cells induced under the AB, AC and ABC conditions have characteristics of typical mesodermal cells.

Next, results showing differences among AB, AC and ABC are shown in FIG. 10C. Since genes that differ between AB and ABC and between AC and ABC but not between AB and AC are considered to be a gene group associated with blood cell differentiation, this gene group was subjected to gene ontology (GO) analysis. The Top 10 GO terms are shown. Among the vascular terms, gene groups associated with the musculoskeletal system and nervous system were confirmed. The rise in gene groups unrelated to blood cell differentiation under the ABC condition suggests that this is the cause of the loss in blood cell differentiation potential.

We also confirmed whether there were differences between the CD43+ blood cells induced under the AB and AC conditions. A gene expression pattern plot is shown in FIG. 10D. Most genes had a fold change of less than 2, and appeared to be extremely similar in both conditions. However, certain genes were more highly expressed under the AB condition than under the AC condition, and a GO analysis showed this gene group to be associated with the immune system. These results suggest that while the blood cells exhibit extremely similar gene expression patterns in the AB and AC groups, there may be a difference in potential related to immune system differentiation.

No Functional Differences in Blood Cells Induced Under Two Conditions

Figure 11:
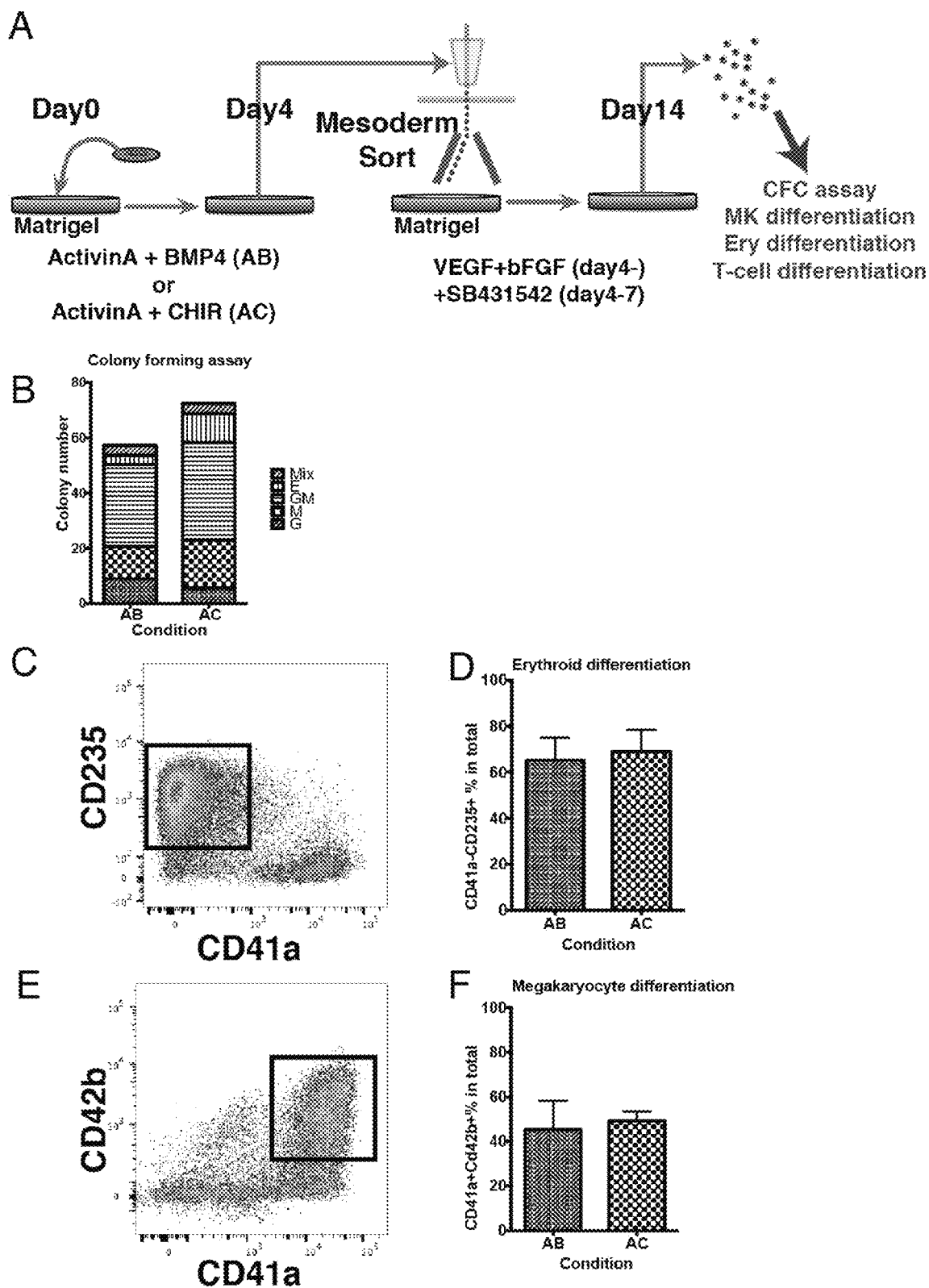

The blood cells induced under the AB and AC conditions exhibited similar gene expression patterns, but with some differences. To test whether this difference affects the functions of the blood cells induced under the two conditions, the hematopoietic cells obtained on day 14 were further differentiated. Specifically, a colony forming ability assay and an in vitro assay of differentiation into erythroblasts, megakaryocytes and T cells were performed as standard functional assays of hematopoietic cells. The results are shown in FIG. 11.

FIG. 11A shows an outline of the experiment. The conditions on days 0 to -4 were divided into AB and AC conditions, and further differentiation was performed using day 14 blood cells induced from the resulting mesoderm.

The results for colony forming ability are shown in FIG. 11B. The blood cells induced under the two conditions had the ability to form multiple kinds of colonies, and there were no significant differences in the types or numbers of the colonies.

Differentiation into erythroblasts, megakaryocytes and T-cells was in accordance with existing reports (Ochi, K. et al. Stem Cells Translational Medicine 3, 792-800 (2014); Takayama, N. & Eto, K.; Nishimura, T. et al. Cell stem Cell 12, 114-126 (2013)). The results for erythroblast differentiation are shown in FIGS. 11C and 11D, the results for megakaryocyte differentiation in FIGS. 11E and 11F, and the results for T-cell differentiation in FIGS. 11G, H and I. Each cell type was detected using unique cell surface markers. Under the erythroblast differentiation conditions CD41a−CD235+ cells were considered erythroblasts, and under the megakaryocyte differentiation conditions, CD41a+CD42b+ cells were considered megakaryocytes. For the T-cells, CD2+CD7+ cells were used as T-cells. When CD4 and CD8 were analyzed simultaneously, all the CD2+CD7+ cells were found to be CD4+CD8+.

When blood cells induced under the two conditions (AB and AC) were compared based on differentiation efficiency into the different cells, no significant differences were found. This suggests that the resulting cells were functionally similar.

These results are shown in FIG. 12. In the presence of Activin A, hematopoietic mesoderm was induced by intervention with either BMP4 or canonical WNT signal, and differentiated efficiently into blood cells under optimal conditions. On the other hand, after intervention with Activin A, BMP4 and canonical WNT signal, the mesodermal system still differentiated into cells but there was a rise in non-blood cell gene groups, and the ability to differentiate into blood cells was lost. The ability to differentiate into the vascular endothelial system was retained under all conditions.

Discussion

Multiple Pathways Discovered by Focusing on Initial Differentiation Steps

In this study, blood cell differentiation lineages were analyzed with hPSC cells to study human developmental processes. As a result, although the importance of major humoral factors was reconfirmed, it was also found for the first time that instead of a single developmental lineage as suggested in many existing reports, blood cells are produced via multiple developmental lineages involving a combination of factors. It was also strongly suggested that control of these lineages is dependent on closely controlling the concentration gradients of the humoral factors.

Figure 2:
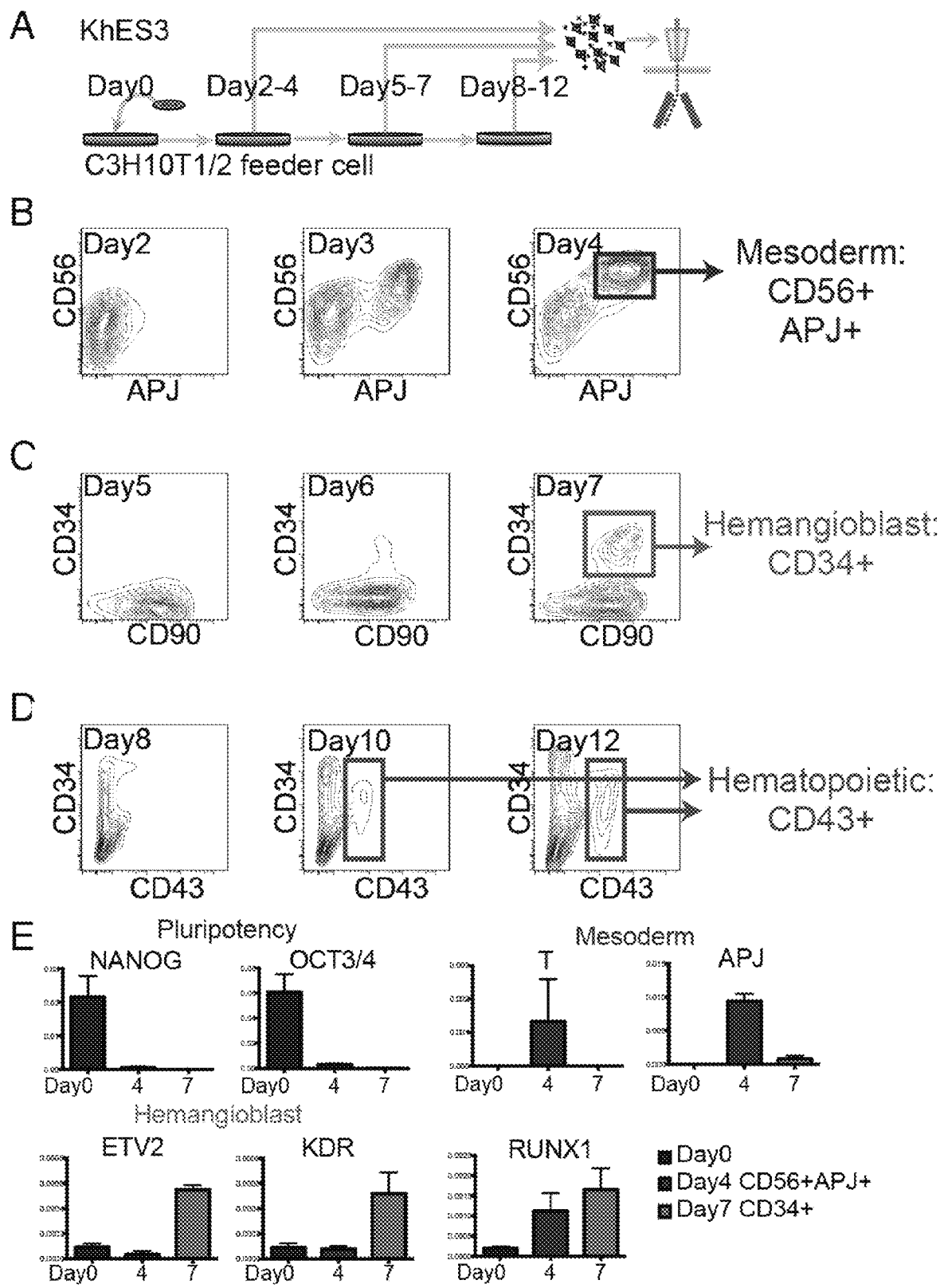
FIG. 2A shows a blood cell differentiation system obtained by co-culturing C3H10T1/2 cells with KhES3, in which the surface antigen expression patterns of collected cells were analyzed in a time series.
FIG. 2B shows the appearance of a CD56+APJ+ cell population in the initial step.
FIG. 2C shows the appearance of a CD34+ cell population in the intermediate step.
FIG. 2D shows the appearance of CD43+ cells in the final step.
FIG. 2E shows the results of a qRT-PCR analysis of the expression patterns of gene groups serving as development stage indicators in each cell population. The results are shown as average values plus standard deviations (n=3).

In mouse development, the interactions of three humoral factor signals—the TGFβ signal, BMP signal and canonical WNT signal—are essential for mesoderm development from epiblasts (which are considered equivalent to pluripotent stem cells). In the region formed as ectoderm, antagonists to these are produced from the visceral endoderm, blocking these signals so that primary intestinal invagination does not occur. In fact, as shown in FIG. 2, addition of a TGFβ signal inhibitor, NOGGIN and a canonical WNT signal inhibitor suppresses and inhibits induction of mesodermal cells. The new finding here is that the inhibitory effects of these three signals are not uniform, and the individual signal strengths greatly influence the fate determination of the differentiation lineage. For example, the TGFβ signal inhibitor had a strong mesoderm differentiation suppressing effect, while the effects of the BMP signal inhibitor and canonical WNT signal inhibitor were limited. With the new, serum-free, feeder-free purified differentiation system developed in the present study, we discovered for the first time that interestingly, introduction of all three signals had the reverse effect of suppressing blood cell differentiation. However, the combinations of two signals (Activin A+BMP4 and Activin A+CHIR99021 (canonical WNT signal)) both efficiently induced blood cell mesoderm populations having blood cell production ability, probably via different lineages.

These results differ from previous reports, and suggest two possibilities: (1) there are differences in molecular mechanisms between the developmental processes of humans and mice, and (2) the existence of similar mechanisms in mice has been overlooked in past studies. There is current interest in the field of interactions between signals, also called signaling crosstalk, and since there have been several reports concerning mesoderm in particular (Singh, A. M. et al. Cell stem Cell 10, 312-326 (2012); Yu, P., Pan, G., Yu, J. & al, Cell stem Cell 8, 326-334 (2011)), it is essential to continue this analysis in further detail by searching for target molecules that merge inside the cells.

There have been almost no reports on detailed investigations into another issue in this field, which is what potential may be demonstrated by induced mesoderm. In fact, the diversity of pluripotent been indicated. In the case of hematopoietic stem cells for example, although all stem cells have the potential to differentiate into blood cells, there are individual differences in differentiation directivity into myeloid and lymphoid lineages (Morita, Y., Ema, H. & Nakauchi, H. Journal of Experimental Medicine 207, 1173-1182 (2010)). Differentiation directivity into megakaryocytes has also been reported from recent studies (Sanjuan-Pla, A. et al. Nature 502, 232-236 (2013)). This phenomenon of hematopoietic stem cell diversity is called heterogeneity, and suggests that cell populations do not necessarily have uniform properties. The same thing needs to be considered with respect to mesoderm, and the possibility needs to be considered that even in initial mesoderm, all mesodermal cells do not necessarily have the same differentiation ability.

New Findings about Unknown Developmental Processes from In Vitro Differentiation System Using hPSC Various combinations and various methods are used in existing blood cell differentiation protocols. In the EB method in particular, isolation and control of individual cells is considered difficult because intercellular interactions are strong. In this sense, experiments involving two-dimensional culture and sparse conditions have contributed to more accurate control of individual cells and the establishment of more stable evaluation systems by standardizing the effects of growth factors and inhibitors. Intercellular interactions themselves can randomly lead to induction of mesoderm with blood cell differentiation potential, and this is thought to influence the redundancy and inconsistency of protocols.

What is the significance of the principal that "multiple pathways exist for the differentiation of one cell", which is one conclusion of this study? For example, redundancy in genes means that multiple molecules play the same role. If a knockout mouse is prepared for one molecule and no change is observed, this may mean that another molecule plays the same role, or that their functions are complementary. The blood cell system is extremely important in the initial stages of development, and a fetus with a mutation that prevents blood cell formation will die in the early embryonic stage. Consequently, the existence of multiple blood cell development pathways is thought to contribute to more stable blood cell production than if there were a single pathway.

The following ideas should also be considered. In findings about mouse development, Nodal, BMP4 and WNT3 expression is important when the primitive streak is formed in the posterior proximal part of the epiblast. However, not enough attention has been paid to what signals are received by each cell as the mesodermal cells sink and migrate after undergoing the epithelial-mesenchymal transition in the primitive streak. Once they become yolk sac mesoderm, these cells may already be fated to become blood cells and vascular endothelium, or to remain mesenchyme, or to become only vascular endothelium. That is, many may have only received signals from 2 out of 3 depending on how they came into contact with expressing cells.

In the experimental results, the effects of signal inputs on days 0 to 4 only appear on day 7 and later. In other words, there is a time delay. This suggests that in order to explain the state of a cell, it is necessary to understand the cell's embryological lineage, or in other words the history of the signals that it has received that determine its fate. It is not necessarily enough to known the current environment of the cell. This information may be stored in the cell outside the genome (epigenomic data).

Reconstruction of Differentiation System and Improvements in Efficiency Match Existing Reports A specific point of this research is that while two kinds of signals may produce a blood cell, three kinds of signals suppress blood cell fate determination. In an existing protocol (Takayama, N. et al. Blood 111, 5298-5306 (2008)), the efficiency of the differentiation induction system was found to be extremely low, since the proportion of CD43+ cells as a percentage of differentiated cells was less than 1% on day 10, all other cells having differentiated into other cell lines (FIG. 3D). Since a maximum of 60% or more of the day 4 CD56+APJ+ cells in the reconstructed differentiation system demonstrated the ability to become blood cells (FIG. 4E), we concluded that there was a problem with intermediate and late stage signals in existing protocols. Protocol improvement was achieved by VEGF, bFGF and TGFβ inhibition. VEGF and bFGF are known as factors that promote vascular endothelial cell growth. The hemangioblast is a concept that has been proposed based on observation of chicken embryos, and is defined as a common progenitor cell of blood cells and blood vessels. In ES cell systems, it is called a blast colony forming cell (BL-CFC). bFGF is essential for BL-CFC induction. bFGF is also believed to induce VEGFR2 expression (Murakami, M. et al. The Journal of clinical investigation 121, 2668-2678 (2011)). Thus, it predicted that these are also active in the specification of hemangioblasts from mesoderm. The TGFβ data are also consistent with past literature (FIG. 3C) (Evseenko, D. et al. P Natl Acad Sci USA 107, 13742-13747 (2010); Wang, C. et al. Cell Res 22, 194-207 (2012)). TGFβ signaling suppresses blood cell production via ALK5 but promotes blood cell production via ALK1, and endoglin is reportedly involved in this (Zhang, L. et al. Blood 118, 88-97 (2011)). Because SB431542 exhibits an ALK5 inhibition effect, it was thought that inhibition of blood cell production was canceled.

Blood cell differentiation was achieved even without feeder cells under conditions that maximized blood cell differentiation efficiency. It was thus possible to finally use a system that allowed mesodermal blood cell production ability to be evaluated. To summarize the essence of this research, it was concluded through verification of the discovered ABC protocols that the fate of developing blood cells is determined by day 4 out of the periods for determining the fates of cell lineages in mesodermal populations.

Although developmental research using human PSC is definitely useful, there is a serious problem of consistency with actual timelines. According to the Carnegie stage classification, blood islands form on the 18th day after fertilization. Because epiblast formation occurs on or after the 7th day after fertilization, the time series are well aligned. However, it is also well known that the blood cell development process is a two-phase process. With the current timing, it is expected that only the initial stage of hematopoiesis is being observed. The hemogenic endothelium present in the ventral part of the dorsal aorta in the AGM region is known as a source of hematopoietic stem cells. Definitive hematopoiesis is generally thought to start from this point. The current observation system and experimental system do not appear to cover the definitive hematopoiesis process. However, the relationship between definitive hematopoiesis and yolk sac hematopoiesis is reportedly continuous rather than interrupted (Samokhvalov, I. M., Samokhvalova, N. I. & Nishikawa, S.-I. Nature 446, 1056-1061 (2007)). The claim of continuity is based on the fact that cells that have been labeled by lineage tracing methods at the yolk sac hematopoiesis stage can be confirmed as labeled blood cells in the adult organism. Moreover, Gata1−Runx1+ cells in ExM have been observed to migrate subsequently to the AGM region (Tanaka, Y. et al. Cell Reports 8, 31-39 (2014)), which also appears to support the principle of continuity. In fact, yolk sac cells exhibit B-cell differentiation when transplanted in vitro and cultured under different conditions from in vivo, and exhibit behavior incompatible with the primitive definition (Tanaka, Y. et al. P Natl Acad Sci USA 109, 4515-4520 (2012)). Considering this, it is difficult to say whether the blood cells obtained in the current experiments are primitive or definitive.

Induction of Hematopoietic Stem Cells

In inducing blood cells from hPSC cells, the ultimate goal of the researchers is the induction of hematopoietic stem cells. Because they are capable of differentiating into all kinds of blood cells, hematopoietic stem cells are used to treat various diseases, especially hematopoietic diseases, and have extremely wide applicability.

Several methods capable of inducing hematopoietic stem cells in mice are known (Kyba, M., Perlingeiro, R. C. R. & Daley, G. Q. Cell 109, 29-37 (2002); Kitajima, K., Minehata, K.-I., Sakimura, K., Nakano, T. & Hara, T. Blood 117, 3748-3758 (2011); Suzuki, N. et al. the journal of the American Society of Gene Therapy 21, 1424-1431 (2013)). It has not been possible to induce hematopoietic stem cells with blood cells induced by manipulating the medium and culture methods. However, induction of hematopoietic stem cells capable of engraftment in mice was achieved by a method of exogenously inducing transcription factors (HoxB4, Lhx2) in induced blood cells. Moreover, when a teratoma is prepared in vivo in a mouse with mouse iPS cells, differentiation of hematopoietic stem cells is induced in the teratoma, and iPS-derived hematopoietic stem cells can be detected in the mouse bone marrow due to homing.

Similarly, it has been reported that cells having hematopoietic stem cell-like activity can be induced in vivo with a teratoma using hPSC cells (Suzuki, N. et al. the journal of the American Society of Gene Therapy 21, 1424-1431 (2013); Amabile, G. et al. Blood 121, 1255-1264 (2012)).

Because these two reports both feature teratoma mediation, they can be said to show that cells having hematopoietic stem cell-like activity, or in other words cells capable of engraftment in immunodeficient mice, can be induced from hPSC. However, when a teratoma is used it is difficult to explain how the hematopoietic stem cells were actually induced. In vitro studies are more desirable from this perspective. There are some reports of in vitro induction of hPSC cells (Wang, L. et al. J. Exp. Med. 201, 1603-1614 (2005); Ledran, M. H. et al. Cell stem Cell 3, 85-98 (2008); Gori, J. L. et al. The Journal of clinical investigation 125, 1243-1254 (2015)). All these methods are different, and at this stage their reproducibility needs to be further studied. Although blood cells induced by the methods used in this study are dramatically improved in terms of induction efficiency, they are unlikely to contain many hematopoietic stem cells since the frequency of mixed colonies was not high in the colony-forming ability assay. There appears to be a need for future transplantation experiments in immunodeficient mice.

In this study, cell characteristics in the early developmental stages that were not clarified in the past were discovered with hPSC cells, and it was shown that multiple conditions may exist for signal requirement in the developmental process. It is often assumed that there is one set of conditions for a particular anatomical structure, but such clear assumptions do not always hold up in practice. The results of this study are not only applicable to blood cells, and it is possible that robust homeostasis is maintained in other organs because they also include such multiple pathways. In addition to their significance for protocols in regenerative medicine, these research results provide evidence for mechanisms of robustness and stability in the developmental process.

What is claimed is:

1. A method for producing hematopoietic mesoderm cells, comprising
    a first step of contacting, for at least 3 days, pluripotent stem cells with (a) Activin A and bone morphogenetic protein 4 (BMP4) in the absence of both basic fibroblast growth factor (bFGF) and one or more CHIRs selected from CHIR-99021 and CHIR-98014, or (b) Activin A and one or more CHIRs selected from CHIR-99021 and CHIR-98014 in the absence of both BMP4 and bFGF, thereby resulting CD56+ and APJ+ cells; and
    a second step of inducing the CD56+ and APJ+ cells to differentiate into CD34+ cells and CD43+ cells by contacting the CD56+ and APJ+ cells with vascular endothelial growth factor (VEGF), bFGF, and a transforming growth factor beta (TGFβ) inhibitor.

2. The method according to claim 1, wherein the first and second steps are performed under serum-free conditions, feeder-free conditions, or both serum-free and feeder-free conditions.

3. A method for producing a culture containing megakaryocytes and megakaryocyte precursor cells, comprising a step of culturing the CD34+ cells and the CD43+ cells according to claim 1 in megakaryocyte differentiation medium to differentiate into a CD41+CD42b+ megakaryocyte population.

4. A method for producing platelets from megakaryocytes produced by the method according to claim 3, which comprises culturing the CD41+CD42b+ megakaryocyte population.

5. The method according to claim 1, wherein the second step is performed under conditions containing serum.

6. The method according to claim 1, wherein the first step is performed under serum-free conditions, feeder-free conditions, or both serum-free and feeder-free conditions, and the second step is performed under conditions containing serum.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Forward primer for Beta-actin (ACTB)

<400> SEQUENCE: 1
tcctccctgg agaagagcta                                          20

<210> SEQ ID NO 2
<211> LENGTH: 18
<212> TYPE: DNA
<213> ORGANISM: Artificial Sequence
<220> FEATURE:
<223> OTHER INFORMATION: Reverse primer for Beta-actin (ACTB)

<400> SEQUENCE: 2
cgtggatgcc acaggact                                            18

<210> SEQ ID NO 3
<211> LENGTH: 20
<212> TYPE: DNA
<213> ORGANISM: Artificial Sequence
<220> FEATURE:
<223> OTHER INFORMATION: Forward primer for NANOG

<400> SEQUENCE: 3
atgcctcaca cggagactgt                                          20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for NANOG

<400> SEQUENCE: 4
cagggctgtc ctgaataagc                                          20

<210> SEQ ID NO 5
<211> LENGTH: 23
<212> TYPE: DNA
<213> ORGANISM: Artificial Sequence
<220> FEATURE:
<223> OTHER INFORMATION: Forward primer for OCT3/4 (POU5F1)

<400> SEQUENCE: 5
gcttcaagaa catgtgtaag ctg                                      23

<210> SEQ ID NO 6
<211> LENGTH: 19
<212> TYPE: DNA
<213> ORGANISM: Artificial Sequence

```
<220> FEATURE:
<223> OTHER INFORMATION: Reverse primer for OCT3/4 (POU5F1)

<400> SEQUENCE: 6
cacgagggtt tctgctttg                                              19

<210> SEQ ID NO 7
<211> LENGTH: 20
<212> TYPE: DNA
<213> ORGANISM: Artificial Sequence
<220> FEATURE:
<223> OTHER INFORMATION: Forward primer for T

<400> SEQUENCE: 7
gctgtgacag gtacccaacc                                             20

<210> SEQ ID NO 8
<211> LENGTH: 21
<212> TYPE: DNA
<213> ORGANISM: Artificial Sequence
<220> FEATURE:
<223> OTHER INFORMATION: Reverse primer for T

<400> SEQUENCE: 8
catgcaggtg agttgtcaga a                                           21

<210> SEQ ID NO 9
<211> LENGTH: 18
<212> TYPE: DNA
<213> ORGANISM: Artificial Sequence
<220> FEATURE:
<223> OTHER INFORMATION: Forward primer for APJ

<400> SEQUENCE: 9
ggcagttctt tgggtgct                                               18

<210> SEQ ID NO 10
<211> LENGTH: 20
<212> TYPE: DNA
<213> ORGANISM: Artificial Sequence
<220> FEATURE:
<223> OTHER INFORMATION: Reverse primer for APJ

<400> SEQUENCE: 10
gtggtgcgta acaccatgac                                             20

<210> SEQ ID NO 11
<211> LENGTH: 20
<212> TYPE: DNA
<213> ORGANISM: Artificial Sequence
<220> FEATURE:
<223> OTHER INFORMATION: Forward primer for ETV2

<400> SEQUENCE: 11
gtggtgcgta acaccatgac                                             20

<210> SEQ ID NO 12
<211> LENGTH: 22
<212> TYPE: DNA
<213> ORGANISM: Artificial Sequence
<220> FEATURE:
<223> OTHER INFORMATION: Reverse primer for ETV2

<400> SEQUENCE: 12
aaggccttct gaatgttctc tg                                          22
```

```
<210> SEQ ID NO 13
<211> LENGTH: 22
<212> TYPE: DNA
<213> ORGANISM: Artificial Sequence
<220> FEATURE:
<223> OTHER INFORMATION: Forward primer for KDR

<400> SEQUENCE: 13
aaggccttct gaatgttctc tg                                            22

<210> SEQ ID NO 14
<211> LENGTH: 23
<212> TYPE: DNA
<213> ORGANISM: Artificial Sequence
<220> FEATURE:
<223> OTHER INFORMATION: Reverse primer for KDR

<400> SEQUENCE: 14
cggaagaaca atgtagtctt tgc                                           23

<210> SEQ ID NO 15
<211> LENGTH: 18
<212> TYPE: DNA
<213> ORGANISM: Artificial Sequence
<220> FEATURE:
<223> OTHER INFORMATION: Forward primer for RUNX1

<400> SEQUENCE: 15
acaaacccac cgcaagtc                                                 18

<210> SEQ ID NO 16
<211> LENGTH: 23
<212> TYPE: DNA
<213> ORGANISM: Artificial Sequence
<220> FEATURE:
<223> OTHER INFORMATION: Reverse primer for RUNX1

<400> SEQUENCE: 16
catctagttt ctgccgatgt ctt                                           23
```